US012799544B2

(12) United States Patent
Saunders et al.

(10) Patent No.: US 12,799,544 B2
(45) Date of Patent: Nov. 17, 2026

(54) **SYSTEMS AND METHODS FOR TARGETING *DIROFILARIA IMMITIS* AND *DIROFILARIA REPENS***

(71) Applicant: Smith College, Northampton, MA (US)

(72) Inventors: Lori J. Saunders, Northampton, MA (US); Steven A. Williams, North Hatfield, MA (US); Nils Pilotte, Feeding Hills, MA (US)

(73) Assignee: Smith College, Northampton, MA (US)

( * ) Notice: Subject to any disclaimer, the term of this patent is extended or adjusted under 35 U.S.C. 154(b) by 947 days.

(21) Appl. No.: 17/605,889

(22) PCT Filed: Apr. 27, 2020

(86) PCT No.: PCT/US2020/030111
§ 371 (c)(1),
(2) Date: Oct. 22, 2021

(87) PCT Pub. No.: WO2020/220030
PCT Pub. Date: Oct. 29, 2020

(65) Prior Publication Data

US 2022/0119894 A1 Apr. 21, 2022

Related U.S. Application Data

(60) Provisional application No. 62/871,463, filed on Jul. 8, 2019, provisional application No. 62/839,136, filed on Apr. 26, 2019.

(51) Int. Cl.
*C12Q 1/68* (2018.01)
*C12Q 1/6893* (2018.01)

(52) U.S. Cl.
CPC ...... *C12Q 1/6893* (2013.01); *C12Q 2600/112* (2013.01)

(58) Field of Classification Search
None
See application file for complete search history.

(56) References Cited

U.S. PATENT DOCUMENTS 6,268,153 B1 * 7/2001 Lizotte-Waniewski ...................... C12Q 1/6888 435/5
6,582,908 B2 * 6/2003 Fodor .................... C07H 21/00 506/30

FOREIGN PATENT DOCUMENTS

CN 106501507 A 3/2017

OTHER PUBLICATIONS

Ahern, Holly, The Scientist, vol. 9, 1995, pp. 1-5.*
Nicholas Vakalis et al., “Improved detection of Dirofilaria repens DNA by direct polymerase chain reaction”, Parasitology International, vol. 48, No. 2, Aug. 1, 1999, pp. 145-150.
Pradeep Ramgapura et al., “Whether Dirofilaria repens parasites from South India belong to zoonotic Candidatus Dirofilaria hongkongensis”, Infections, Genetics and Evolution, vol. 67, Oct. 26, 2018, pp. 121-125.
Mariana Silva Sousa et al., “Performance of an Ultra-Sensitive Assay Targeting the Circulating Anodic Antigen (CAA) for Detection of Schistosoma mansoni Infection in Low Endemic Area in Brazil”, Frontiers in Immunology, vol. 10, Apr. 4, 2019, Art. 682, pp. 1-16.
Achinya Phuakrod et al., “Diagnosis of feline filariasis assisted by a novel semi-automated microfluidic device in combination with high resolution melting real-time PCR”, Parasites & Vectors, vol. 12, No. 1, Apr. 8, 2019. pp. 1-9.
European Patent Office, International Search Report and Written Opinion for PCT application No. PCT/US2020/030111, Oct. 19, 2020 (27 pages).

* cited by examiner

*Primary Examiner* — Jehanne S Sitton
(74) *Attorney, Agent, or Firm* — Merchant & Gould P.C.

(57) ABSTRACT

Platforms, including devices, systems, kits, and methods, are provided for the differential detection of *Dirofilaria immitis* and *Dirofilaria. repens* in an animal host using parasite-specific DNA target capture techniques as well as polymerase chain reaction detection of those targets.

16 Claims, 13 Drawing Sheets

Specification includes a Sequence Listing.

Fig. 1B

Dre1 First Strand (SEQ ID NO:5)

5′ TTGGTAATAAGACTTAATAAATTTTAATCTCAAATATTTCCTTGTTAATATATCTGGTGTTCTATTGTTATATATATTCCGGTAGACCATGAAATGATGTTTTTAT ...

Biotinylated Forward Capture Oligonucleotide (SEQ ID NO:7)

Biotin—TCCTTGTTAATATATCTGGTGTTCTA

Dre1 Second Strand (SEQ ID NO:6)

3′ AACCATTATTCTGAATTATTTAAAATTAGAGTTTATAAAGGAACAATTATATAGACCACAAGATAACAATATATATAAGGCCATCTGGTACTTTACTACAAAAATA ...

... TATTGTACATTATCAAACTCTGGTAAACCAAATGTCCAAGAACCGATGCATTAAATGAAAACAGAAACCTTGGTAATAAGACTTAATAAATTTTAATCTCAAATA 3′

CATTTGGTTTACAGGTTCTTGG—Biotin

Biotinylated Reverse Capture Oligonucleotide (SEQ ID NO:8)

... ATAACATGTAATAGTTTGAGACCATTTGGTTTACAGGTTCTTGGCTACGTAATTTACTTTTGTCTTTGGAACCATTATTCTGAATTATTTAAAATTAGAGTTTAT 5′

Fig. 3B

*Dirofilaria immitis* Repeat Sequence in Tandem

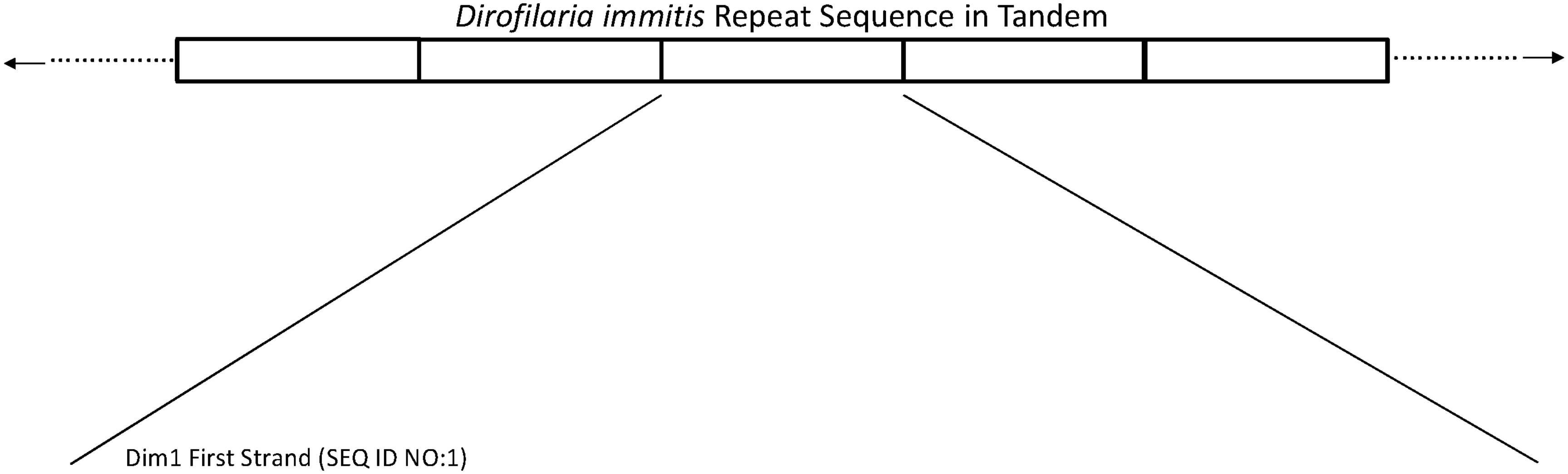

Dim1 First Strand (SEQ ID NO:1)

5′ ACGATGAATTTGTCGTATATATTTGTATAATTCATAGA TACGCATTGTGACTCGTCTAATCATATATATAT 3′

TATCTATGCGTAACACTGAGC

Reverse Primer (SEQ ID NO:21)

Forward Primer (SEQ ID NO:9)

ACGATGAATTTGTCGTATATATTTGT

Probe (SEQ ID NO:22)

ACGCATTGTGACTCGTCTAATCAT

3′ TGCTACTTAAACAGCATATATAAACATATTAAGTATCT ATGCGTAACACTGAGCAGATTAGTATATATATA 5′

Dim1 Second Strand (SEQ ID NO:2)

*Dirofilaria immitis* Repeat Sequence in Tandem

Fig. 3D

*Dirofilaria repens* Repeat Sequence in Tandem

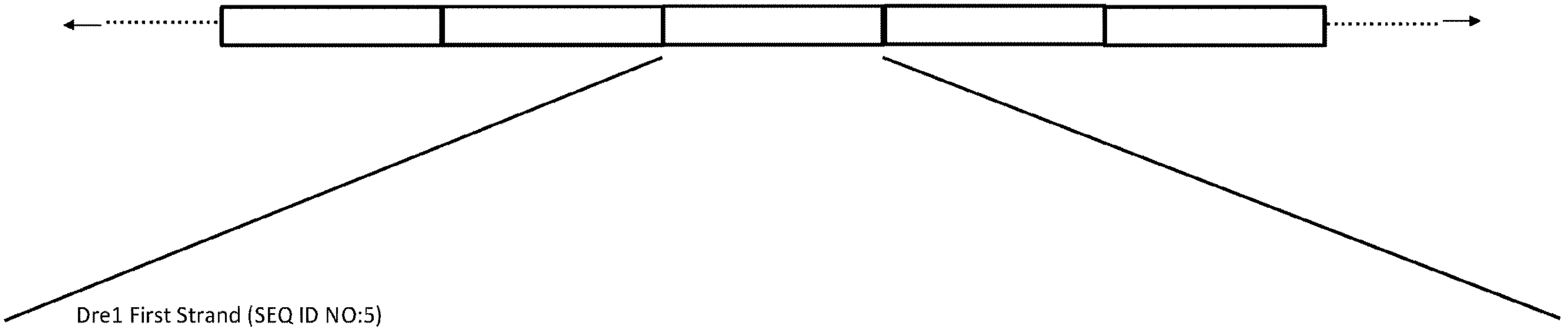

Dre1 First Strand (SEQ ID NO:5)

5′ TTGGTAATAAGACTTAATAAATTTTAATCTCAAATATTTCCTTGTTAATATATCTGGTGTTCTATTGTTATATATATTCCGGTAGACCATGAAATGATGTTTTTAT ...

Forward Primer (SEQ ID NO:12)

TCCTTGTTAATATATCTGGTGTTCTA

Probe (SEQ ID NO:14)

TATATTCCGGTAGACCATGAAATGATGTTT

3′ AACCATTATTCTGAATTATTTAAAATTAGAGTTTATAAAGGAACAATTATATAGACCACAAGATAACAATATATATAAGGCCATCTGGTACTTTACTACAAAAATA ...

... TATTGTACATTATCAAACTCTGGTAAACCAAATGTCCAAGAACCGATGCATTAAATGAAAACAGAAACCTTGGTAATAAGACTTAATAAATTTTAATCTCAAATA 3′

CATTTGGTTTACAGGTTCTTGG

Reverse Primer (SEQ ID NO:13)

... ATAACATGTAATAGTTTGAGACCATTTGGTTTACAGGTTCTTGGCTACGTAATTTACTTTTGTCTTTGGAACCATTATTCTGAATTATTTAAAATTAGAGTTTAT 5′

Dre1 Second Strand (SEQ ID NO:6)

Fig. 3E

*Dirofilaria repens* Repeat Sequence in Tandem

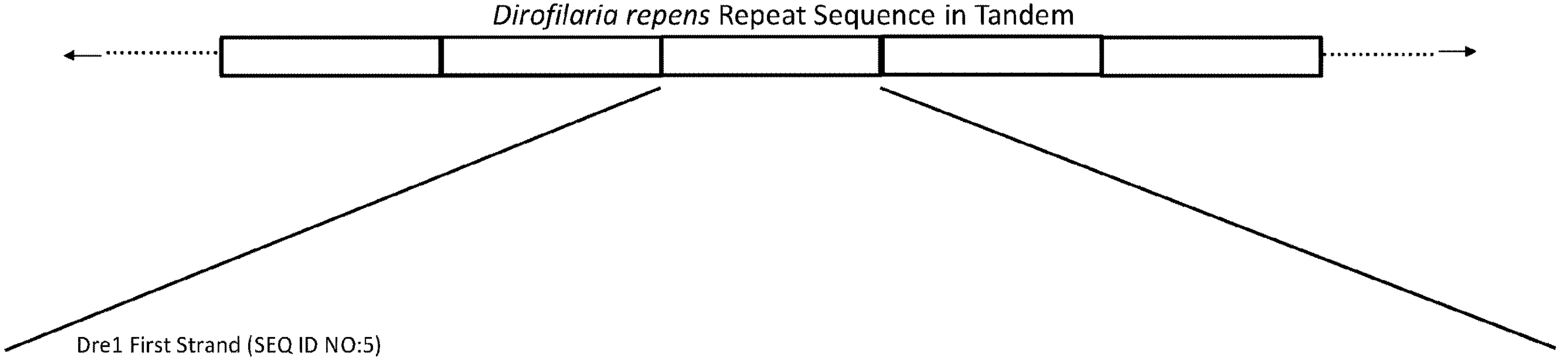

Dre1 First Strand (SEQ ID NO:5)

5′ TTGGTAATAAGACTTAATAAATTTTAATCTCAAATATTTCCTTGTTAATATATCTGGTGTTCTATTGTTATATATATTCCGGTAGACCATGAAATGATGTTTTTAT ...

Forward Primer (SEQ ID NO:15)

TTCCGGTAGACCATGAAATG

3′ AACCATTATTCTGAATTATTTAAAATTAGAGTTTATAAAGGAACAATTATATAGACCACAAGATAACAATATATATAAGGCCATCTGGTACTTTACTACAAAAATA ...

... TATTGTACATTATCAAACTCTGGTAAACCAAATGTCCAAGAACCGATGCATTAAATGAAAACAGAAACCTTGGTAATAAGACTTAATAAATTTTAATCTCAAATA 3′

TTTGTCTTTGGAACCATTATTCTG

Reverse Primer (SEQ ID NO:16)

Probe (SEQ ID NO:17)

CATTATCAAACTCTGGTAAACCAAATGTCC

... ATAACATGTAATAGTTTGAGACCATTTGGTTTACAGGTTCTTGGCTACGTAATTTACTTTTGTCTTTGGAACCATTATTCTGAATTATTTAAAATTAGAGTTTAT 5′

Dre1 Second Strand (SEQ ID NO:6)

Fig. 3F

*Dirofilaria repens* Repeat Sequence in Tandem

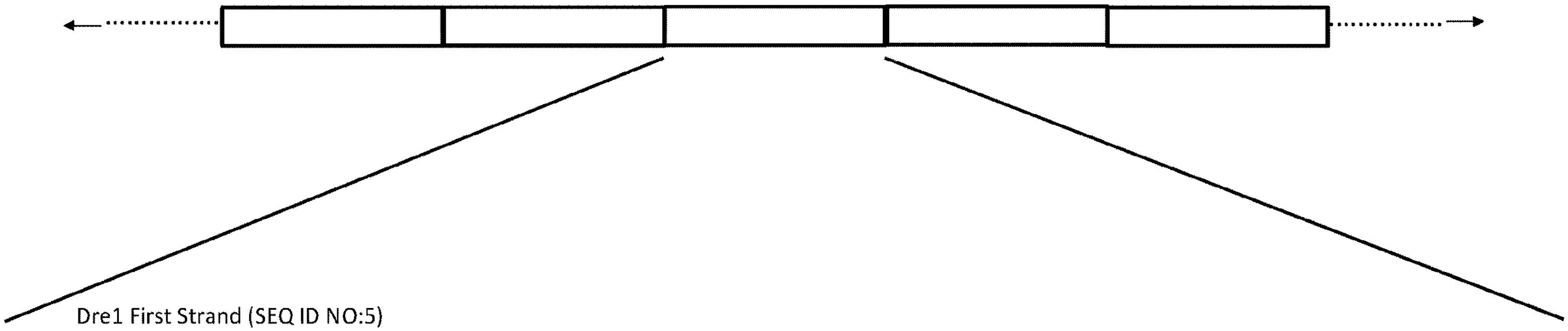

Dre1 First Strand (SEQ ID NO:5)

5′ TTGGTAATAAGACTTAATAAATTTTAATCTCAAATATTTCCTTGTTAATATATCTGGTGTTCTATTGTTATATATATTCCGGTAGACCATGAAATGATGTTTTTAT ...

Forward Primer (SEQ ID NO:18)

CTATTGTTATATATATTCCGGTAGACCA

3′ AACCATTATTCTGAATTATTTAAAATTAGAGTTTATAAAGGAACAATTATATAGACCACAAGATAACAATATATATAAGGCCATCTGGTACTTTACTACAAAAATA ...

... TATTGTACATTATCAAACTCTGGTAAACCAAATGTCCAAGAACCGATGCATTAAATGAAAACAGAAACCTTGGTAATAAGACTTAATAAATTTTAATCTCAAATA 3′

TTACAGGTTCTTGGCTACG

Reverse Primer (SEQ ID NO:19)

Probe (SEQ ID NO:20)

ATTGTACATTATCAAACTCTGGTAAACCA

... ATAACATGTAATAGTTTGAGACCATTTGGTTTACAGGTTCTTGGCTACGTAATTTACTTTTGTCTTTGGAACCATTATTCTGAATTATTTAAAATTAGAGTTTAT 5′

Dre1 Second Strand (SEQ ID NO:6)

SYSTEMS AND METHODS FOR TARGETING *DIROFILARIA IMMITIS* AND *DIROFILARIA REPENS*

CROSS-REFERENCE TO RELATED APPLICATIONS

This application is a U.S. national phase entry of International Application No. PCT/US2020/030111 filed Apr. 27, 2020, which claims the benefit of U.S. Provisional Application No. 62/839,136 filed Apr. 26, 2019, and U.S. Provisional Application No. 62/871,463 filed Jul. 8, 2019, each of which is hereby incorporated herein by reference in its entirety.

TECHNICAL FIELD

The present invention relates to systems and methods for identifying infection by parasites in an animal host, and, in particular, infection by *Dirofilaria immitis* and *Dirofilaria repens.*

BACKGROUND ART

Dog heartworm disease, and to a lesser extent cat heartworm disease, is due to infection by the parasitic roundworm *Dirofilaria immitis*. [Haddock, K. C. Soc. Sci. Med. (1987); Knight, D. H. *Veterinary Clinics of North America—Small Animal Practice* (1987); Shearer, P. *Banf Appl. Res. Knowl. Team* 1-16 (2011)]. Heartworm disease is one of the most significant health problems of companion animals in the United States and worldwide [Wang, D. et al. *Parasites and Vectors* 7, 1-18 (2014); Dantas-Torres, F. and Otranto D. *Parasites and Vectors* 6, 1 (2013)]. The parasite is also known to infect other mammals including wolves, coyotes, bears, foxes, sea lions, seals, and the critically endangered North American black-footed ferret. *D. immitis* also occasionally infects humans, although it rarely causes significant clinical manifestations [Ro, J. Y. et al. *Human Pathology* (1989)]. *D. immitis* is most prevalent in North and South America, Europe, Japan and Australia.

*Dirofilaria repens* is a parasitic roundworm closely related to *D. immitis* that also causes disease in dogs, cats, wolves, coyotes, foxes, sea lions, and humans [Genchi, C. and Kramer, L. *Parasites and Vectors* 10, 1-6 (2017)]. *D. repens* causes a variety of clinical manifestations in dogs including significant dermatitis of various types, skin nodules and, in severe cases, organ damage [Capelli, G. et al. *Parasites and Vectors* 11, 1-21 (2018)]. *D. repens* is an Old World disease found primarily in Europe, Africa, and southern Asia [Genchi, C. and Kramer, L. H. *Vet. Parasitol.* 280, 108995 (2019)]. Like *D. immitis, D. repens* is also transmitted by mosquitoes. Also, like *D. immitis, D. repens* occasionally causes infections in humans [Capelli, G. et al. *Parasites and Vectors* 11, 1-21 (2018); Harizanov, R. N. et al. *Parasitol. Res.* 113, 1571-1579 (2014)].

Ideally, all dogs and cats, both pets and strays, should be tested for the presence of *D. immitis*, preferably on a periodic basis. Such a test is particularly important if the host mammal is to be placed on a prophylactic drug regimen. Testing currently includes direct observation of microfilariae in the blood, antigen testing, and the polymerase chain reaction ("PCR") [Trancoso, T. A. L. et al. *Rev Bras Parasitol Vet.* 29, 1, (2020)]. Direct observation of microfilariae in the blood using a microscope is the oldest test, but suffers from a lack of sensitivity because low levels of microfilariae are often missed or because microfilariae are not present in the blood despite the presence of adult worms in the host mammal's body (due to single-sex infections, worms not yet sexually mature, worms too old to reproduce, or the host mammal's immune system being successful at killing microfilariae but not adult worms). In addition, direct microscopic evaluation of the blood for mass-screening of large population of host mammals is not practical due to the time and skill-level required.

Currently, the most commonly used tests for screening dogs for *D. immitis* are antigen tests based on the detection of circulating *D. immitis* antigen shed into the bloodstream from sexually mature adult female worms [Little, S. et al. *Parasites and Vectors* 11, 1-10 (2018); Ciuca, L. et al. *Vet. Parasitol.* 225, 81-85 (2016)]. There are a few significant problems with antigen-based tests. First, the test does not effectively detect *D. immitis* parasites in the mammalian host until the female parasites are sexually mature (6-7 months following infection). This is a critical period because the delay in detection gives the parasites a head start, whereas if treatment could be started early, the parasites would have less time to cause harm to the host animal and the treatment efficacy would be much improved. Furthermore, antigen-based tests will not effectively detect single-sex male infections. In addition, about 1% of the host mammals that test antigen negative have been shown to be microfilariae positive (false negative results). Finally, there is substantial evidence that the antigen-based assay can cross-react with other parasite species and cause false positive results [Schnyder, M. and Deplazes, P. *Parasit Vectors.* 5, 258 (2012); Aroch, I. et al. *Vet Parasitol.* 211, 303-305 92015)].

A few DNA-based PCR tests have been developed to address the issues with microscopy-based testing and antigen-based tests [Gioia, G. et al. *Vet. Parasitol.* 172, 160-163 (2010); Norgen Biotek. *Dirofilaria immitis* PCR Detection Kit (2011); Latrofa, M. S. et al. *Vet. Parasitol.* 185, 181-185 (2012); Albonico, F. et al. *Vet. Parasitol.* 200, 128-132 (2014); Tahir, D. et al. *Vet. Parasitol.* 235, 1-7 (2017)]. However, all of these PCR tests have been designed to detect low copy number DNA targets found in the genome of *D. immitis* and/or *D. repens*, and are therefore not highly sensitive. Due to an inability of these tests to detect very low-level or pre-patent infections, i.e., infections prior to the time during which *D. immitis* or *D. repens* infections can be detected using serological antigen tests, e.g., infections prior to female adult worms being sexually mature and producing microfilariae, these tests have been used sparingly or not at all in the veterinary setting.

The rationale for a highly sensitive species-specific test for *D. repens* is similar to that for *D. immitis*. With *D. repens*, microscopy-based tests are primarily used to look for the presence of microfilariae [Capelli, G. et al. *Parasites and Vectors* 11, 1-21 (2018)]. There is no standardized antigen-based test available for screening host mammals that is specific for *D. repens* [Ciucă, L. et al. *Vet. Parasitol.* 225, 81-85 (2016)]. Thus, there is a significant need for a highly sensitive species-specific assay that can detect small amounts of DNA in blood or serum of a host mammal for the presence of *D. immitis* and/or *D. repens* at all life cycle stages.

No highly sensitive species-specific PCR test has been developed for detecting *D. immitis* or *D. repens* in mosquito hosts. Nevertheless, knowledge of the geographic distribution and density of *D. immitis* and *D. repens* in the mosquito population is an important factor in planning parasite control programs. One must be able to accurately assess the geographic distribution of infected mosquitoes in order to understand the degree of risk to local dog and cat populations. Thus, there is a need for a highly sensitive species-specific test for detecting *D. immitis* and *D. repens* at any life cycle stage in pools of mosquitoes collected in the field.

SUMMARY OF THE EMBODIMENTS

In accordance with one embodiment of the invention, a device for diagnosis of a parasite infection in an animal host, the device including a PCR measurement apparatus, having a thermocycler. The PCR measurement apparatus is configured to target a repetitive sequence in DNA of the parasite in a tissue sample obtained from the infected animal host.

The parasite may be *Dirofilaria immitis* or *Dirofilaria repens* and the repetitive sequence may be selected to provide sensitivity and selectivity to the parasite. In some embodiments, the PCR measurement apparatus includes an optical readout mechanism and the optical readout mechanism optionally includes a test strip having a visible band.

The tissue sample can be plasma, serum, or whole blood obtained from the infected animal host. Additionally, the tissue sample can be from an infected mosquito.

In accordance with an embodiment of the invention, a method of treating a mammalian host suspected of being infected with a parasite is provided. The method includes (a) providing a sample from the mammalian host suspected of being infected with the parasite; and (b) causing detecting presence of the parasite in the sample. The detecting includes (i) making DNA available from the sample; (ii) mixing the sample with a labeled DNA complementary to a target DNA; and (iii) detecting the target DNA using PCR; wherein, if the presence of the parasite has been detected as a result of causing detecting, administrating to the mammalian host a treatment effective at reducing or eliminating the parasite infection.

The labeled DNA has been made using processes including (a) identifying the target DNA, wherein the target DNA is repetitive DNA uniquely possessed by the parasite. The identifying includes (i) obtaining genomic DNA sequence reads from the parasite, (ii) trimming each sequence read to produce a read set of trimmed sequence reads of equal length, (iii) comparing each sequence of the read set to all of the other sequence reads in the read set in order to form read pairs, wherein each read of a given pair shares with the other read of the pair at least 90% similarity over at least 55% of its length, (iv) evaluating the read pairs to identify in the genome of the parasite a candidate set of sequences having putatively a high copy number in the genome, and (v) selecting from the candidate set of sequences a final sequence uniquely possessed by the parasite; and (b) causing synthesis of the labeled DNA using the final sequence uniquely possessed by the parasite, wherein the labeled DNA is complementary to the identified repetitive DNA uniquely possessed by the parasite.

The parasite may be *D. immitis* or *D. repens*. In some embodiments, the parasite infection is patent. In other embodiments, the parasite infection is pre-patent. The tissue sample may be plasma, serum, or whole blood obtained from the infected mammalian host, which may be a canine.

In some embodiments, the labeled DNA includes a conjugation moiety. The conjugation moiety can be biotin. In some embodiments, the target DNA is isolated from the mixture using a capture medium that binds a capture DNA. The capture medium can lie a magnetic bead or a test strip and the capture medium may be coated with streptavidin.

In some embodiments, the PCR is real-time PCR using a primer and probe set. In some embodiments, the parasite is *D. immitis* and the primer and probe set is selected from the group consisting of p1Dim1, p2Dim1, and p3Dim1. In other embodiments, the parasite is *D. repens* and the primer and probe set is selected from the group consisting of p1Dre1, p2Dre1, and p3Dre1.

In some embodiments, the parasite is *D. immitis* and the target DNA is Dim1. The labeled DNA can be a set of capture oligonucleotides consisting of SEQ ID NO:3 and SEQ ID NO:4.

In some embodiments, the parasite is *D. repens* and the target DNA is Dre1. The labeled DNA can be a set of capture oligonucleotides consisting of SEQ ID NO:7 and SEQ ID NO:8.

In some embodiments, the treatment is selected from the group consisting of melarsomine, ivermectin, doxycycline, moxidectin, and combinations thereof.

In accordance with an embodiment of the invention, a kit is provided for detecting a parasite infection in an animal host. The kit includes (a) labeled DNA complementary to repetitive species-specific parasite target DNA, (b) a capture medium that binds a capture DNA, and (c) a set of written instructions for detecting the parasite infection.

The parasite can be *D. immitis* or *D. repens* and the labeled DNA includes a conjugation moiety. In some embodiments, the conjugation moiety is biotin and the capture medium is selected from the group consisting of a magnetic bead, a test strip, and combinations thereof. In some embodiments, the capture medium is coated with streptavidin. The kit may include a primer and probe set.

In some embodiments, the parasite is *D. immitis* and the labeled DNA is a set of capture oligonucleotides consisting of SEQ ID NO:3 and SEQ ID NO:4. In some embodiments, the parasite is *D. immitis* and the target DNA is Dim1. In some embodiments, the parasite is *D. immitis* and the primer and probe set is selected from the group consisting of p1Dim1, p2Dim1, p3Dim1, and p4Dim1.

In other embodiments, the parasite is *D. repens* and the labeled DNA is a set of capture oligonucleotides consisting of SEQ ID NO:7 and SEQ ID NO:8. In some embodiments, the parasite is *D. immitis* and the target DNA is Dre1. In some embodiments, the parasite is *D. repens* and the target DNA is Dre1. In some embodiments, the parasite is *D. repens* and the primer and probe set is selected from the group consisting of p1Dre1, p2Dre1, and p3Dre1.

BRIEF DESCRIPTION OF THE DRAWINGS

The foregoing features of embodiments will be more readily understood by reference to the following detailed description, taken with reference to the accompanying drawings, in which:

FIGS. 1A and 1B show *D. immitis* and *D. repens* repetitive target DNA and exemplary biotinylated capture oligonucleotides in accordance with embodiments of the present invention. FIG. 1A shows *D. immitis* Dim1 repetitive target DNA and exemplary Dim1 capture oligonucleotides hybridized to the target DNA. FIG. 1B shows *D. repens* Dre1 repetitive target DNA and exemplary Dre1 capture oligonucleotides hybridized to the target DNA. All forward capture oligonucleotides are 5' to 3'. All reverse capture oligonucleotides are 3' to 5'.

FIGS. 3A to 3F show exemplary primer and probe sets for real-time PCR of *D. immitis* repetitive target DNA Dim1 and *D. repens* repetitive target DNA Dre1 in accordance with embodiments of the present invention. FIGS. 3A-3C show exemplary real-time PCR primer and probe sets p1Dim1, p2Dim1, and p3Dim1, respectively, hybridized to *D. immitis* repetitive target DNA Dim1. FIGS. 3D-3F show exemplary real-time PCR primer and probe sets p1Dre1, p2Dre1, and p3Dre1, respectively, hybridized to *D. repens* repetitive target DNA Dern. All forward primers and probes are 5' to 3'. All reverse primers are 3' to 5'. All probes of exemplary primer and probe sets p1Dim1, p2Dim1, p3Dim1, p1Dre1, p2Dre1, and p3Dre1 have the fluorescent dye 6-carboxyfluorescein ("6-FAM") attached to their 5' terminus, the quencher Iowa Black® FQ ("IABkFQ") attached to their 3' terminus, and an internal ZEN™ quencher 9 bases from the 5' end.

FIG. 6A shows test strip PCR results of a control dilution series of *D. immitis* genomic DNA. FIGS. 6B and 6C show test strip PCR results for *D. immitis* infected and uninfected canines.

DETAILED DESCRIPTION OF SPECIFIC EMBODIMENTS

Figure 1A:
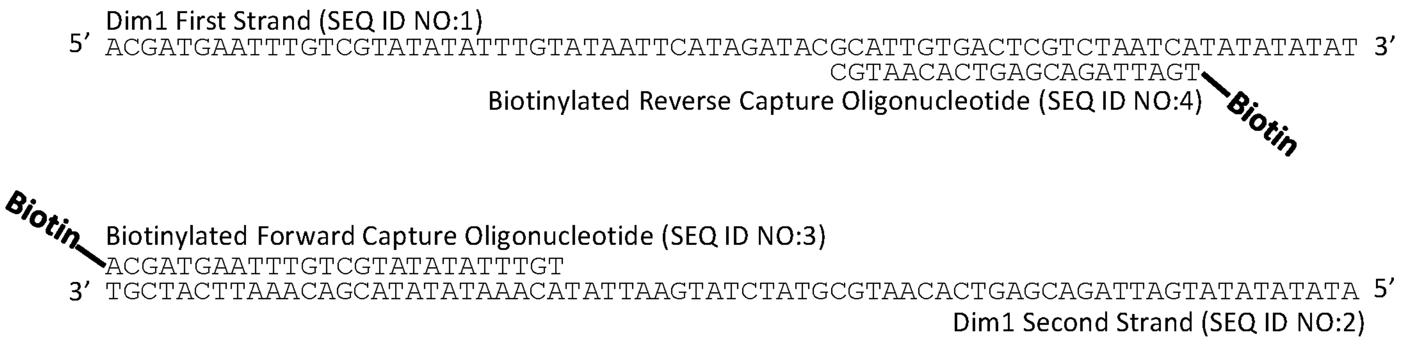

Definitions. As used in this description and the accompanying claims, the following terms shall have the meanings indicated, unless the context otherwise requires:

A "set" includes at least one member.

As used herein, "real-time polymerase chain reaction," "real-time PCR," "quantitative polymerase chain reaction," and "qPCR" are synonymous.

A "thermocycler" is an apparatus configured to amplify segments of DNA via a polymerase chain reaction (PCR) by running a series of cycles of temperature changes that cause replication of the DNA. See, e.g., Mullis K B (April 1990) *Scientific American*. 262 (4): 56-61, 64-5. See also Saiki R et al. (December 1985) *Science*. 230 (4732): 1350-4.

An "accompanying optical readout mechanism" is a system including a set of DNA-binding labeled sequence-specific primers and probes, in combination with a mechanism for reporting optically on the presence of a threshold when a quantification cycle Cq has been reached by an associated thermocycler. The optical readout mechanism may be achieved by using fluorescently labeled sequence-specific primers and probes and photo-optic detectors as in standard qPCR systems, as available, for example from Applied Biosystems (ThermoFisher, Waltham, Massachusetts, USA). Alternatively, the optical readout mechanism may be implemented by using suitably labeled DNA to trigger appearance of a visible band on a test strip, as described in Zaky W I et al. (2018)*PLoS Negl Trop Dis* 12(11): e0006962.

A "configured PCR measurement apparatus" is a PCR measurement apparatus equipped with primers directed to a specific DNA target.

As used herein, "infected," e.g., an infected animal host, an infected mammalian host, or an infected mosquito host, shall mean that an organism harbors parasite *D. immitis* or *D. repens* in its body.

"Pre-patent infections," and the like, shall mean *D. immitis* or *D. repens* infections occurring prior to the time during which *D. immitis* or *D. repens* infections can be detected using serological antigen tests.

"Patent infections," and the like, shall mean *D. immitis* or *D. repens* infections occurring after the time during which *D. immitis* or *D. repens* infections can be detected using serological antigen tests.

"Conjugation moiety" shall mean a chemical moiety attached to a nucleic acid molecule that facilitates the binding of the nucleic acid molecule to a capture medium, such as a magnetic bead, non-magnetic bead, membrane, test strip (utilized during strip tests), or contents of a column.

"Capture DNA" shall mean a member of the group consisting of (a) a capture oligonucleotide having a conjugation moiety, (b) DNA synthesized from a PCR primer having a conjugation moiety, and (c) combinations thereof.

"Capture medium" shall mean any medium that specifically binds to a particular conjugation moiety. For example, magnetic bead, non-magnetic bead, membrane, test strip (utilized during strip tests), and contents of a column, may be coated with molecules, proteins, or other reactive groups that interact with and bind a particular conjugation moiety. Capture oligonucleotides having a conjugation moiety, or DNA synthesized from a PCR primer having a conjugation moiety, can bind to a capture medium.

"Labeled DNA" shall mean a member selected from the group consisting of (a) a capture oligonucleotide having a conjugation moiety, (b) a PCR primer having a conjugation moiety; (c) a real-time PCR probe comprising one or more moieties for facilitating its detection, (d) a test strip probe comprising one or more moieties for facilitating its detection, and (e) and combinations thereof.

"Mammalian host" shall mean a mammal that is infected with a parasite.

"Mosquito host" and "mosquito vector" shall mean a mosquito that is infected with a parasite.

"Animal host" or "host" that is not qualified as being a mammalian host or a mosquito host, includes both mammalian hosts and mosquito hosts.

"Complementary" shall mean that at least 80% of the bases of an oligonucleotide, primer, or probe are capable of base pairing with a target sequence.

For both *D. immitis* and *D. repens*, infection begins when infective larvae (third stage L3) are deposited by a mosquito on the skin of the mammalian host. The infective larvae enter through the bite wound caused by the mosquito and burrow into the subcutaneous tissue. During the next 6-7 months, *D. immitis* larvae molt twice, migrate to the pulmonary arteries and heart, and develop to become fully adult parasites. Unlike *D. immitis, D. repens* adult worms stay in the subcutaneous tissue and do not migrate to the heart or pulmonary arteries.

Adult male and female worms mate and the females release thousands of microfilariae (first stage L1 larvae) into the blood stream each day. These microfilariae circulate in the blood until picked up by a mosquito while ingesting a blood meal. Once in the mosquito, the L1 larvae molt to L2 and then to infectious L3 larvae. The L3 migrate to the mosquito's mouth parts where they can infect another mammalian host when the mosquito feeds again. Thus, the complete life cycle of both *D. immitis* and *D. repens* requires both a mammalian host and a mosquito host [Kotani, T. and Powers, K. G. *Am. J. Vet. Res.* 43, 2199-2206 (1982); Silaghi, C., Beck, R. et al. *Parasites and Vectors* 10, 1-13 (2017)]. In infected mammalian hosts, the adult worms attain a length of 10-12 inches and can live for 5-10 years.

Microfilariae can live in the bloodstream for 2-3 years prior to being taken up by a mosquito during a blood meal.

In mammalian hosts infected with *D. immitis*, visible symptoms include labored breathing, coughing and exhaustion. Damage to the heart, lung, and kidneys often occurs before symptoms are observed [Monchy, D., Levenes, H., Guegan, H., Poey, C. & Dubourdieu, D. Pulmonary dirofilariasis. *Médecine tropicale: revue du Corps de santé colonial* (1993)]. Often, the mammalian host will eventually die due to congestive heart failure.

Various drugs can be used to treat heartworm disease including melarsomine, which can kill the adult worms. However, such treatment is expensive because hospitalization is recommended and, in many cases, forced rest is required for many months. Before and after melarsomine treatment, other drugs are used and in some cases the melarsomine treatment may need to be repeated. This treatment is not without risk since killed adult heartworms and microfilariae can result in blood clots which can lodge in the lungs and circulation. In many cases, especially advanced cases where the chronic symptoms are already apparent at the time of diagnosis, the disease is still fatal even with treatment due to the increased risk of blood clots and other complications. In such advanced cases, or where the animal cannot withstand the melarsomine treatment, surgery may be required to physically remove the adult heartworms from the pulmonary arteries and heart. Thus, prevention of the initial infection is a much-preferred alternative since it is both safer and significantly less expensive. Although the risk of infection can be dramatically reduced by keeping the pet indoors, this is often not a practical or desirable approach. Administration of a prophylactic drug such as ivermectin on a monthly basis to at risk animals is the most common approach to heartworm prevention. Such preventative treatments should only be initiated after a diagnostic test for the presence of heartworm. Even when using the monthly preventative prophylactic, periodic testing for *D. immitis* is still recommended to insure the treatment is working properly and to detect any infection that may have been present, but not detected, before treatment began.

Other treatments for *D. immitis* infections include pretreatment with ivermectin and doxycycline prior the use of melarsomine in order to reduce pulmonary harm caused by the heartworms. *D. immitis* infections may also be directly treated with macrocyclic lactones, e.g., ivermectin and moxidectin, along with doxycycline.

Although the clinical manifestations of *D. repens* are different from *D. immitis*, drug treatment regimens are similar, although less standardized.

Described herein are platforms, including devices, systems, kits, and methods, for the differential detection of *D. immitis* and *D. repens* through the coupling of parasite-specific DNA target capture techniques and polymerase chain reaction ("PCR") detection of those targets in accordance with embodiments of the present invention. In some embodiments, PCR is real-time PCR. Because of their high sensitivity and species-specificity, these platforms can be used to screen mammalian host blood/plasma samples to detect infections of either *D. immitis* or *D. repens* as early as 10 weeks post-infection. In accordance with embodiments of the present invention, patent infections and pre-patent infections may be detected by allowing for the selective capture of genomic target DNA or cell-free target DNA ("cfDNA").

In some embodiments, platforms described herein are capable of detecting pre-patent infections of *D. immitis* or *D. repens*. Platforms for detecting these pre-patent infections are not presently available. However, the ability to detect pre-patent infections would be clinically useful, opening the door for new treatment strategies, because the infected animal may be treated early with a lower dose of medication, may experience less treatment side effects, and may suffer less physiological damage due to the infection.

In some embodiments, the platforms described herein are intended for use by veterinarians and clinical laboratories to enable early detection of *D. immitis* or *D. repens* infection. In some embodiments, these platforms may also be used by epidemiologists, facilitating the screening and analysis of mosquitoes, the insect vectors of these parasites. Mosquito screening will enable mapping, evaluation of treatment strategies, evaluation of intervention programs, and assessment of risk for community spread of *D. immitis* and *D. repens* infections.

Parasite detection platforms described herein were developed through sophisticated bioinformatics-based screening of the genomes of both *D. immitis* and *D. repens*. For each organism, bioinformatics screening identified the genomic DNA sequence that was predicted to be both unique to the organism and present at greatest copy number within the parasite's genome. These DNA elements represent the optimal targets for the detection of their respective parasites because they are both unique to their species of origin and highly repetitive within their genome of origin, making them species-specific and optimally sensitive detection assay targets. These repetitive DNA elements are sensitive targets for DNA detection assays because the greater the number of targets, the more sensitive the assay. By designing oligonucleotide constructs with sequence complementarity to these assay targets, oligonucleotides that are capable of binding their specific genomic target sequences may be used to capture DNA molecules comprising the identified target sequences.

In some embodiments, the addition of a biotin-label, (a conjugation moiety) to each capture molecule allows for the attachment of these artificial constructs to a magnetic bead coated with streptavidin via a biotin-streptavidin linkage. This linkage results in the generation of capture beads capable of specifically binding (hybridizing) to *D. immitis* or *D. repens* target DNA within the blood/serum of a mammalian host or from mosquitoes. Following specific binding and capture of the target DNA, *D. immitis* and/or *D. repens* target DNA may be enriched via magnetic bead isolation and elution from the capture oligonucleotides.

In some embodiments, capture oligonucleotides may first be hybridized to the target DNA, and then be bound to an appropriately treated capture medium, e.g., streptavidin-coated beads. In other embodiments, the capture oligonucleotides are first bound to an appropriately treated capture medium, followed by hybridization to the target DNA.

Other than the biotin/streptavidin interaction, various chemistries may be used to bind capture DNA to appropriate capture media. In some embodiments, capture DNA may be modified with a 5' sulfhydryl conjugation moiety that facilitates the direct binding of capture DNA to capture beads such as Dynabeads™ M-270 Amine (ThermoFisher, Waltham, Massachusetts, USA), or other similarly coated capture media. In other embodiments, capture oligonucleotides may be modified with a 5' or 3' amino conjugation moiety, or PCR primers may be labeled with a 5' amino conjugation moiety, that facilitates the direct binding of the capture DNA via an amide bond to capture beads such as Dynabeads™ M-270 Carboxylic Acid (ThermoFisher, Waltham, Massachusetts, USA), which are coated with carboxylic acid, or other similarly coated capture media.

In some embodiments, an I-Linker™ conjugation moiety may be attached to the 5' end of the capture oligonucleotide(s) or PCR primers. The I-Linker™ conjugation moiety may substitute for amino conjugation moiety modifications in many applications. Additionally, the I-Linker™ conjugation moiety expands the range of capture medium reactive groups that may be used for binding of the capture DNA to the capture medium. For example, aldehyde- and ketone-modified capture media may be used to bind capture DNA having the I-Linker™ conjugation moiety.

In some embodiments, amine-modified capture DNA may be bound to a capture medium via exposed carboxylate groups or succinimidyl esters on the capture medium. In other embodiments, thiol-modified capture DNA may be bound to an aminosilane capture medium using a reagent cross-linker, such as succinimidyl 4-(maleimidophenyl)butyrate (SMPB). In some embodiments, Acrydite™ may be used as a conjugation moiety to covalently bind capture DNA to a capture medium through acrylic linkages. In other embodiments, a 5' digoxigenin NHS ester may be used as a conjugation moiety to bind capture DNA to capture media coated with anti-digoxigenin. In other embodiments, 5' sulfhydryl-modified capture DNA may be used to bind to amine-coated capture media.

Carboxyl and amino conjugation moieties are common reactive groups for binding capture DNA to capture media. For example, capture media comprising the following reactive groups may be utilized: —COOH (carboxylic acid), —$RNH_2$ (primary aliphatic amine), —$ArNH_2$ (aromatic amine), —$ArCH_2Cl$ chloromethyl (vinyl benzyl chloride), —$CONH_2$ (amide), —$CONHNH_2$ (hydrazide), —CHO (aldehyde), —OH (hydroxyl), —SH (thiol), and —COC (epoxy).

Other capture media capable of binding capture oligonucleotides may also be used, such as non-magnetic beads, e.g., silica beads, polystyrene beads, Sepharose™ beads, and Sephadex® beads. These beads may be isolated using centrifugation followed by elution of the target DNA. In addition, column-based capture of the target DNA may be carried out by using columns packed with the aforementioned non-magnetic beads coated with the capture oligonucleotides. Columns may also be packed with magnetic beads coated with the capture oligonucleotides. A sample may run through such a column and if any target DNA is present, it will bind to the capture oligonucleotide-coated beads. Target DNA can subsequently be eluted from these beads.

As further described below, test strips may also be used as capture media to bind to DNA synthesized from a PCR primer having a conjugation moiety.

Other target DNA capture methods may include microfluidic lateral flow techniques using capture oligonucleotides attached to a surface (membranes). Microarray-like slides or polystyrene microwells coated with capture oligonucleotides may also be used to capture the target DNA.

In some embodiments, elution of the target DNA occurs by simply heating the capture beads or other capture media, thereby breaking the interactions (hydrogen bonds) between the capture oligonucleotides and the captured target molecules possessing sequences complementary to the capture oligonucleotides. The supernatant, containing these thermally released target molecules is then recovered to enable downstream testing by PCR.

Elution of the target DNA may also be performed by conducting 3-5 cycles of PCR on bead-bound target DNA to amplify the target DNA into solution. Amplified target DNA can then be subject to detection via downstream testing by PCR. In addition, denaturing reagents, e.g., alkylating reagents that result in a pH greater than 11 in the DNA-containing solution, may also be used to disrupt the hydrogen bonds between the capture oligonucleotides and the captured target molecules possessing sequences complementary to the capture oligonucleotides.

Figure 2:
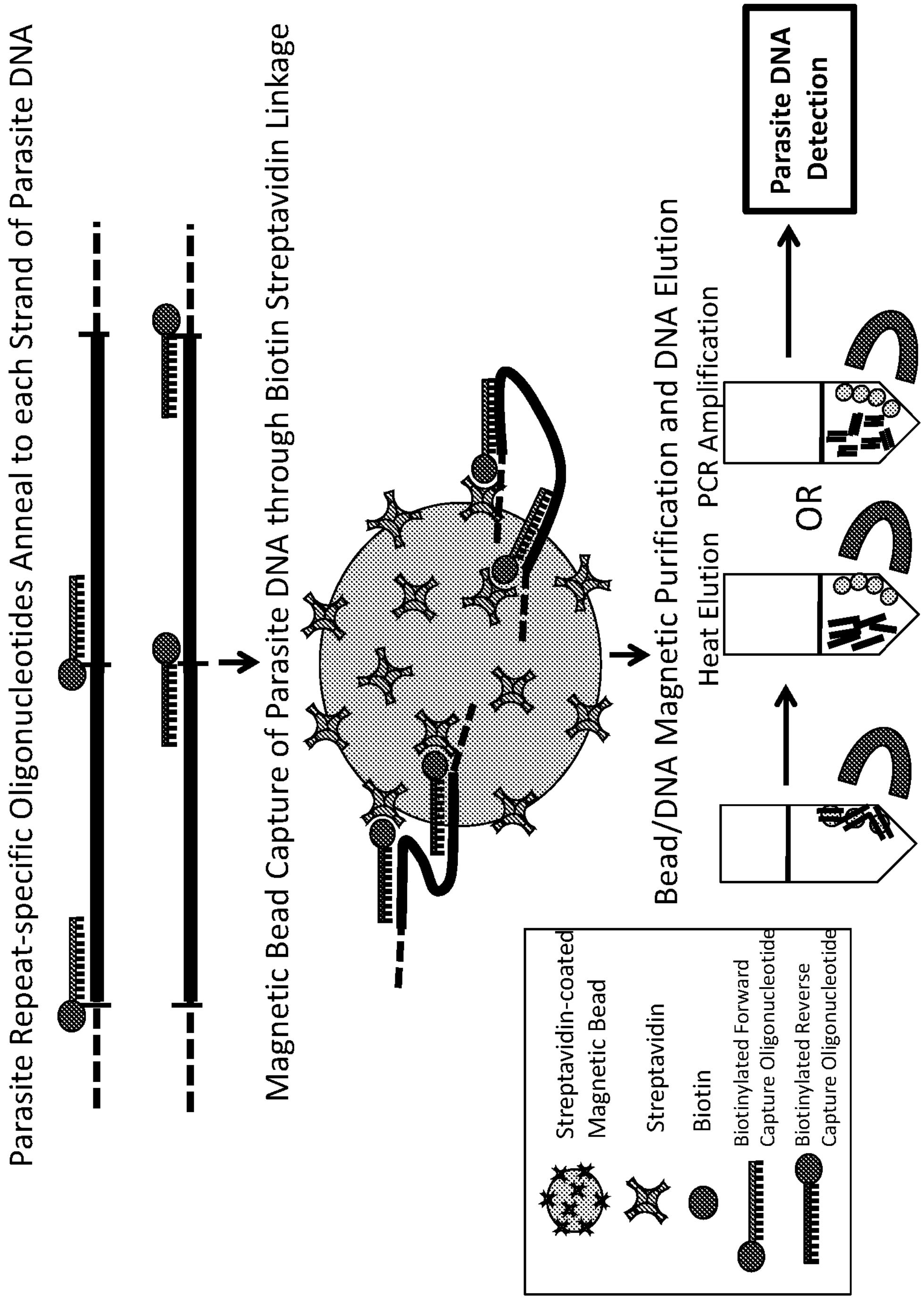
FIG. 2 shows exemplary illustration of a target DNA capture procedure using biotinylated capture oligonucleotides and streptavidin-coated magnetic beads in accordance with an embodiment of the present invention.

Exemplary capture oligonucleotides are illustrated in FIG. 1A and FIG. 1B. The repetitive species-specific DNA sequences used to design these capture oligonucleotides are also illustrated in FIG. 1A and FIG. 1B. An exemplary illustration of a target DNA capture procedure is shown in FIG. 2.

In some embodiments, following isolation of target DNA from a sample via complementary sequence capture, magnetic pull down, and thermal release, highly sensitive species-specific detection of *D. immitis* and/or *D. repens* may be achieved by using PCR-based assays on the isolated DNA sample. PCR-based assays were developed by exploiting the same sensitive and species-specific repetitive DNA elements targeted for capture. In some embodiments, for each parasite, PCR primers were designed to amplify these target DNA sequences, and a modified real-time PCR probe construct was designed to enable fluorescence detection following amplification.

Preferably, each PCR primer and probe is from 12 base pairs (bp) to 40 bp in length. Although primers and probes need not be perfectly complementary to their target sequences, at least 80% of the bases of an oligonucleotide, primer, or probe are capable of base pairing with a target sequence.

Figure 3A:
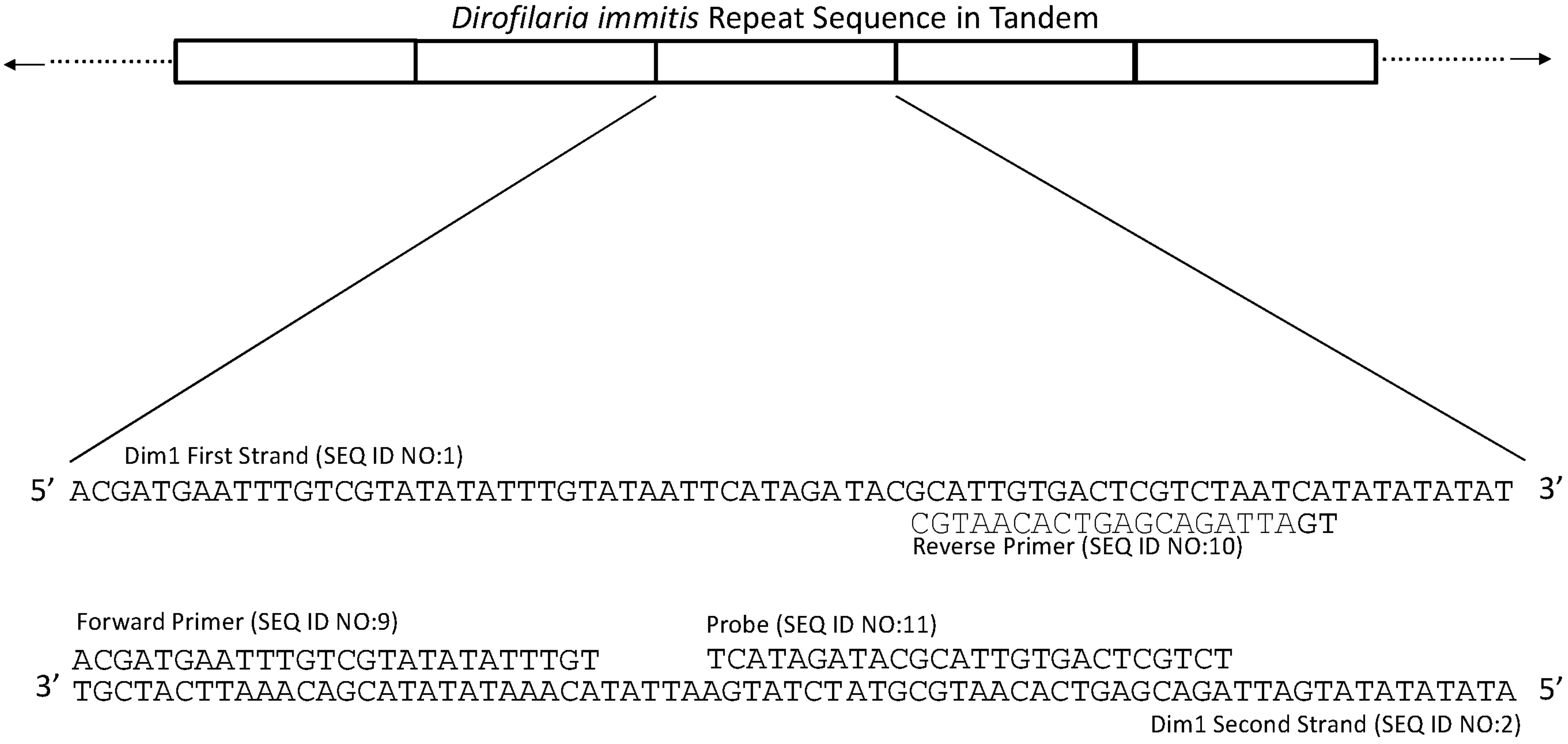

In some embodiments, the probe design includes a 6-FAM fluorophore, i.e., a fluorescent dye, linked to the 5' end of the construct, a non-fluorescent quencher linked to the 3' end of the construct, and incorporation of an internal non-fluorescent quencher. Exemplary primer and probe constructs are illustrated in FIG. 3A and FIG. 3D.

Various real-time PCR probes may be utilized, which comprise a fluorophore, i.e., a fluorescent dye, and one or two quenchers.

Suitable probe fluorophores include, but are not limited to, 5' 6-FAM, 5' TET, 5' Yakima Yellow®, 5' HEX, 5' JOE, 5' Cy3, 5' Texas Red-X®, 5' Cy5, 5' MAX, 5' TYE 563, 5' TAMRA, 5' ROX. 5' TEX 615, and 5' TYE 665.

In various embodiments of the present invention, appropriate quenchers, as would be readily apparent to one of skill in the art, are also combined with the aforesaid probe fluorophores. These quenchers include, but are not limited to, ZEN™ (an internal quencher) plus 3' Iowa Black FQ®, 3' Iowa Black RQ-Sp®, TAO™ (an internal quencher) plus Iowa Black RQ-Sp®, and Black Hole Quencher 1. See, e.g., Integrated DNA Technologies (Coralville, Iowa, USA) and Silaghi C. et al. *Parasit Vectors.* 10, 1, (2017). TAMRA quenchers or MGB-NFQ quenching chemistry may also be used (ThermoFisher Scientific (Waltham, Massachusetts, USA)).

Various types of real-time PCR probes may be utilized. For example, 5' nuclease probes, may be used, e.g., PrimeTime qPCR Probes (Integrated DNA Technologies (Coralville, Iowa, USA)). 5' exonuclease probes are not initially fluorescent because the probe fluorophore is quenched by one or two quenchers. However, during PCR amplification, the 5' exonuclease activity of DNA polymerase releases the quencher(s) from close proximity to the probe fluorophore, allowing for the detection of a probe fluorophore fluorescence. Higher signal-to-noise ratios can be achieved by using internal quenchers, e.g., ZEN™ and TAO™ quenchers, along with a 3' quencher. Although internal quenchers may be located at any internal position within a probe, preferably, the internal quencher is 9 bases from the probe fluorophore at the 5' end.

Probes that utilize modified nucleotides may also be used. For example, Affinity Plus qPCR Probes (Integrated DNA Technologies (Coralville, Iowa, USA)) incorporate several locked nucleic acid (LNA) nucleotides into the probe in order to give the probe higher structural stability and increased $T_m$, which may lead to greater specificity. In addition, PrimeTime LNA qPCR Probes (Integrated DNA Technologies (Coralville, Iowa, USA)), which utilize one or more LNAs, may be used in order to give the probe higher structural stability for short probes and increased $T_m$, which may lead to greater specificity.

Molecular beacon real-time PCR probes may also be used. Unlike 5' nuclease probes, molecular beacon probes have self-complementary ends that form a quenched, hairpin structure when not bound to their target sequence. Molecular beacon probes comprise a fluorophore at one end and a quencher at the other end. Fluorescent signal is generated by the linearization of the probe upon hybridization to its target sequence during real-time PCR cycling.

In its most typical form, DNA exists as a double-stranded molecule consisting of a first strand and a second strand. The sequence of each of these strands is the reverse complement of the other and each strand is base-paired with the other strand. In some embodiments, both strands of the repetitive species-specific target DNA are captured by oligonucleotides complementary to a sequence or sequences present on each strand, and, in some embodiments, are amplified and detected using PCR. Preferably, the sequences of the capture oligonucleotides are the same as the sequences of the PCR primers, in order to prevent false positive amplification or reduced real-time PCR efficiency. In other embodiments, a single strand of the repetitive species-specific target DNA is captured by an oligonucleotide complementary to a sequence present on the strand, and is amplified and detected using PCR. Preferably, the sequence of the capture oligonucleotide is the same as the sequence of one of the PCR primers.

In some embodiments, test samples, including potentially infected blood/serum samples from dogs and cats, or mosquito samples potentially harboring parasites, are processed to facilitate the release of pathogen-derived target DNA if present. Target DNA is then captured, isolated, and detected using PCR. Capture of target DNA, e.g., using magnetic beads, will occur only when a sample contains *D. immitis* or *D. repens* DNA and a positive real-time PCR signal will occur only following capture of the target DNA. In some embodiments, less than 5 copies of captured target DNA may be detected. It is estimated that a single *D. immitis* microfilaria contains 10 million copies of the exemplary target DNA element shown in FIG. 1A. It is estimated that a single *D. repens* microfilaria contains 30 million copies of the exemplary target DNA shown in FIG. 1B. Furthermore, the genomic target DNA that is captured, isolated, and detected, is present at all life stages, allowing for the detection of both pre-patent and patent infections, as well as male-only, female-only and mixed male and female infections.

The described nucleic acid constructs are oligonucleotides or oligonucleotide derivatives specific for *D. immitis* or *D. repens*. Exemplary capture oligonucleotides for *D. immitis* (SEQ ID NO:4 and SEQ ID NO:3) complementary to the first strand (the *D. immitis* "target sequence") (SEQ ID NO:1) and second strand (SEQ ID NO:2) of exemplary target DNA element Dim1, respectively, are shown in FIG. 1A.

Exemplary capture oligonucleotides for *D. repens* (SEQ ID NO:8 and SEQ ID NO:7) complementary to the first strand (SEQ ID NO:5) (the *D. repens* "target sequence") and second strand (SEQ ID NO:6) of exemplary target DNA element Dre1, respectively, are shown in FIG. 1B. Other, *D. repens* target sequences are also provided. For example, SEQ ID NO:25 may be utilized in accordance with embodiments of the present invention. In some embodiments, SEQ ID NO:26 may be used as a target sequence. However SEQ ID NO:26 has some similarity with *Brugia malayi* DNA. *D. repens*-specific target sequences SEQ ID NO:27, and SEQ ID NO:28 may also be utilized in accordance with embodiments of the invention.

Figure 3C:
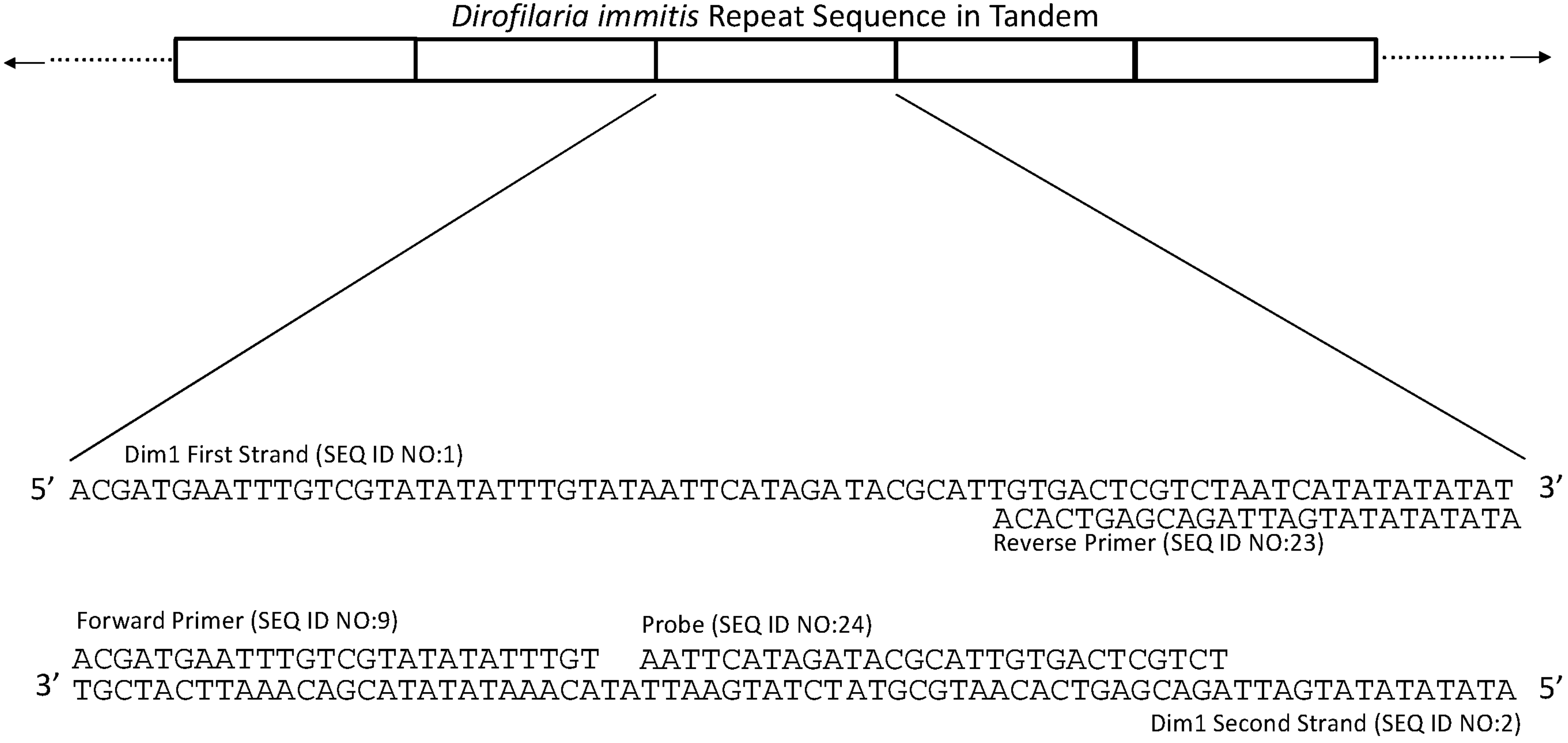

Exemplary primer and probe set p1Dim1 for *D. immitis* (primers SEQ ID NO:9 and SEQ ID NO:10, and probe SEQ ID NO:11) is shown in FIG. 3A. Exemplary primer and probe set p2Dim1 for *D. immitis* (primers SEQ ID NO:9 and SEQ ID NO:21, and probe SEQ ID NO:22) is shown in FIG. 3B. Exemplary primer and probe set p3Dim1 for *D. immitis* (primers SEQ ID NO:9 and SEQ ID NO:23, and probe SEQ ID NO:24) are shown in FIG. 3C.

Exemplary primer and probe set p1Dre1 for *D. repens* (primers SEQ ID NO:12 and SEQ ID NO:13, and probe SEQ ID NO:14) is shown in FIG. 3D. Exemplary primer and probe set p2Dre1 for *D. repens* (primers SEQ ID NO:15 and SEQ ID NO:16, and probe SEQ ID NO:17) is shown in FIG. 3E. Exemplary primer and probe set p3Dre1 for *D. repens* (primers SEQ ID NO:18 and SEQ ID NO:19, and probe SEQ ID NO:20) is shown in FIG. 3F.

In some embodiments, *D. immitis* capture oligonucleotides and primer and probe sets p1Dim1, p2Dim1, p3Dim1, and p4Dim1, were designed based on output sequence data obtained from the next-generation sequencing (NGS)-based analyses of adult male and female *D. immitis* genomic DNA (see Materials and Methods, below).

In some embodiments, *D. repens* capture oligonucleotides and primer and probe sets p1Dre1, p2Dre1, and p3Dre1, were designed based on output sequence data obtained from the NGS-based analysis of adult male and female *D. repens* genomic DNA (see Materials and Methods, below).

In some embodiments, a set of capture oligonucleotides (one capture oligonucleotide for each strand of the double-stranded target DNA) is provided for the most abundant and species-specific genomic target DNA element of *D. immitis*, and is effective for isolating *D. immitis*-derived target DNA from samples originating from mammalian host or mosquito vector species and enriching the resulting samples for this target DNA. For example, exemplary biotinylated capture oligonucleotides SEQ ID NO:3 and SEQ ID NO:4, or derivatives thereof, may be used to capture both strands of target DNA Dim1. In some embodiments, a single capture oligonucleotide for capturing a single strand of the target DNA may be used. For example, one exemplary biotinylated capture oligonucleotide selected from the group consisting of SEQ ID NO:3 and SEQ ID NO:4, or derivatives thereof, may be used to capture one strand of target DNA Dim1.

In some embodiments, a set of capture oligonucleotides (one capture oligonucleotide for each strand of the double-stranded target DNA) is provided for the most abundant and species-specific genomic target DNA element of *D. repens*, and is effective for isolating *D. repens*-derived target DNA from a sample originating from mammalian host or mosquito vector species and enriching the resulting samples for this target DNA. For example, exemplary biotinylated capture oligonucleotides SEQ ID NO:7 and SEQ ID NO:8, or derivatives thereof, may be used to capture both strands of target DNA Dre1. In some embodiments, a single capture oligonucleotide for capturing a single strand of the target DNA may be used. For example, one exemplary biotinylated capture oligonucleotide selected from the group consisting of SEQ ID NO:7 and SEQ ID NO:8, or derivatives thereof, may be used to capture one strand of target DNA Dre1.

In some embodiments, an optimal primer and probe set is provided that is effective in a real-time PCR assay for detecting the presence of *D. immitis* target DNA in a sample derived from a mammalian host or mosquito vector species. Detection of the target DNA indicates that that the mammalian host or mosquito vector species is infected with *D. immitis*. For example, in some embodiments, exemplary primer and probe set p1Dim1, constituting primers SEQ ID NO:9 and SEQ ID NO:10, or derivatives thereof, and probe SEQ ID NO:11, or a derivative thereof, may be used. In other embodiments, exemplary primer and probe set p2Dim1, constituting primers SEQ ID NO:9 and SEQ ID NO:21, or derivatives thereof, and probe SEQ ID NO:22, or a derivative thereof, may be used. In some embodiments, exemplary primer and probe set p3Dim1, constituting primers SEQ ID NO:9 and SEQ ID NO:23, or derivatives thereof, and probe SEQ ID NO:24, or a derivative thereof, may be used.

In some embodiments, an optimal primer and probe set is provided that is effective in a real-time PCR assay for detecting the presence of *D. repens* target DNA in a sample derived from a mammalian host or mosquito vector species. Detection of the target DNA indicates that that the mammalian host or mosquito vector species is infected with *D. repens*. For example, in some embodiments, exemplary primer and probe set p1Dre1, constituting primers SEQ ID NO:12 and SEQ ID NO:13, or derivatives thereof, and probe SEQ ID NO:14, or a derivative thereof, may be used. In other embodiments, exemplary primer and probe set p2Dre1, constituting primers SEQ ID NO:15 and SEQ ID NO:16, or derivatives thereof, and probe SEQ ID NO:17, or a derivative thereof, may be used. In some embodiments, exemplary primer and probe set p3Dre1, constituting primers SEQ ID NO:18 and SEQ ID NO:19, or derivatives thereof, and probe SEQ ID NO:20, or a derivative thereof, may be used.

In some embodiments, a method of treating a mammalian host suspected of being infected with a parasite is provided. The method includes (a) providing a sample from the mammalian host suspected of being infected with the parasite; and (b) causing detecting presence of the parasite in the sample. The detecting includes (i) making DNA available from the sample; (ii) mixing the sample with a labeled DNA complementary to a target DNA; and (iii) detecting the target DNA using PCR; wherein, if the presence of the parasite has been detected as a result of causing detecting, administrating to the mammalian host a treatment effective at reducing or eliminating the parasite infection.

The labeled DNA has been made using processes including (a) identifying the target DNA, wherein the target DNA is repetitive DNA uniquely possessed by the parasite. The identifying includes (i) obtaining genomic DNA sequence reads from the parasite, (ii) trimming each sequence read to produce a read set of trimmed sequence reads of equal length, (iii) comparing each sequence of the read set to all of the other sequence reads in the read set in order to form read pairs, wherein each read of a given pair shares with the other read of the pair at least 90% similarity over at least 55% of its length, (iv) evaluating the read pairs to identify in the genome of the parasite a candidate set of sequences having putatively a high copy number in the genome, and (v) selecting from the candidate set of sequences a final sequence uniquely possessed by the parasite; and (b) causing synthesis of the labeled DNA using the final sequence uniquely possessed by the parasite, wherein the labeled DNA is complementary to the identified repetitive DNA uniquely possessed by the parasite.

The parasite may be *D. immitis* or *D. repens*. In some embodiments, the parasite infection is patent. In other embodiments, the parasite infection is pre-patent. The tissue sample may be plasma, serum, or whole blood obtained from the infected mammalian host, which may be a canine.

In some embodiments, the labeled DNA includes a conjugation moiety. The conjugation moiety can be biotin. In some embodiments, the target DNA is isolated from the mixture using a capture medium that binds a capture DNA. The capture medium can be a magnetic bead or a test strip and the capture medium may be coated with streptavidin.

In some embodiments, the PCR is real-time PCR using a primer and probe set. In some embodiments, the parasite is *D. immitis* and the primer and probe set is selected from the group consisting of p1Dim1, p2Dim1, and p3Dim1. In other embodiments, the parasite is *D. repens* and the primer and probe set is selected from the group consisting of p1Dre1, p2Dre1, and p3Dre1.

In some embodiments, the parasite is *D. immitis* and the target DNA is Dim1. The labeled DNA can be a set of capture oligonucleotides consisting of SEQ ID NO:3 and SEQ ID NO:4.

In some embodiments, the parasite is *D. repens* and the target DNA is Dre1. The labeled DNA can be a set of capture oligonucleotides consisting of SEQ ID NO:7 and SEQ ID NO:8.

In some embodiments, the treatment is selected from the group consisting of melarsomine, ivermectin, doxycycline, moxidectin, and combinations thereof.

In some embodiments, kits are provided for detecting a parasite infection in an animal host, The kit includes (a) labeled DNA complementary to repetitive species-specific parasite target DNA, (b) a capture medium that binds a capture DNA, and (c) a set of written instructions for detecting the parasite infection.

The parasite can be *D. immitis* or *D. repens* and the labeled DNA includes a conjugation moiety. In some embodiments, the conjugation moiety is biotin and the capture medium is selected from the group consisting of a magnetic bead, a test strip, and combinations thereof. In some embodiments, the capture medium is coated with streptavidin. The kit may include a primer and probe set.

In some embodiments, the parasite is *D. immitis* and the labeled DNA is a set of capture oligonucleotides consisting of SEQ ID NO:3 and SEQ ID NO:4. In some embodiments, the parasite is *D. immitis* and the target DNA is Dim1. In some embodiments, the parasite is *D. immitis* and the primer and probe set is selected from the group consisting of p1Dim1, p2Dim1, p3Dim1, and p4Dim1.

In other embodiments, the parasite is *D. repens* and the labeled DNA is a set of capture oligonucleotides consisting of SEQ ID NO:7 and SEQ ID NO:8. In some embodiments, the parasite is *D. immitis* and the target DNA is Dre1. In some embodiments, the parasite is *D. repens* and the target DNA is Dre1. In some embodiments, the parasite is *D. repens* and the primer and probe set is selected from the group consisting of p1Dre1, p2Dre1, and p3Dre1.

In some embodiments a device is provided for diagnosis of *D. immitis* or *D. repens* infection in an animal host, the device comprising a PCR measurement apparatus, including a thermocycler, the PCR measurement apparatus configured to target a repetitive target sequence in DNA of *D. immitis* or *D. repens* in a tissue sample obtained from the infected animal host. The repetitive target sequence may be selected to provide sensitivity and selectivity to *D. immitis* or *D. repens*. The PCR measurement apparatus may include an optical readout mechanism. The optical readout mechanism optionally includes a test strip having a visible band. The tissue sample may be from the infected animal host. The tissue sample may be from an infected mosquito or infected canine.

In some embodiments, a PCR-based platform utilizing a test strip is provided for detection of a parasite infection, such as a *D. immitis* or *D. repens* infection, in an animal host. See generally, Zaky et al. *PLoS Negl Trop Dis.* 2018 Nov. 21; 12(11). This strip test platform utilizes test strip as a capture medium. The test strip has a band coated with a reactive group for binding to DNA that has been synthesized via PCR using a PCR having a conjugation moiety.

Figure 5:
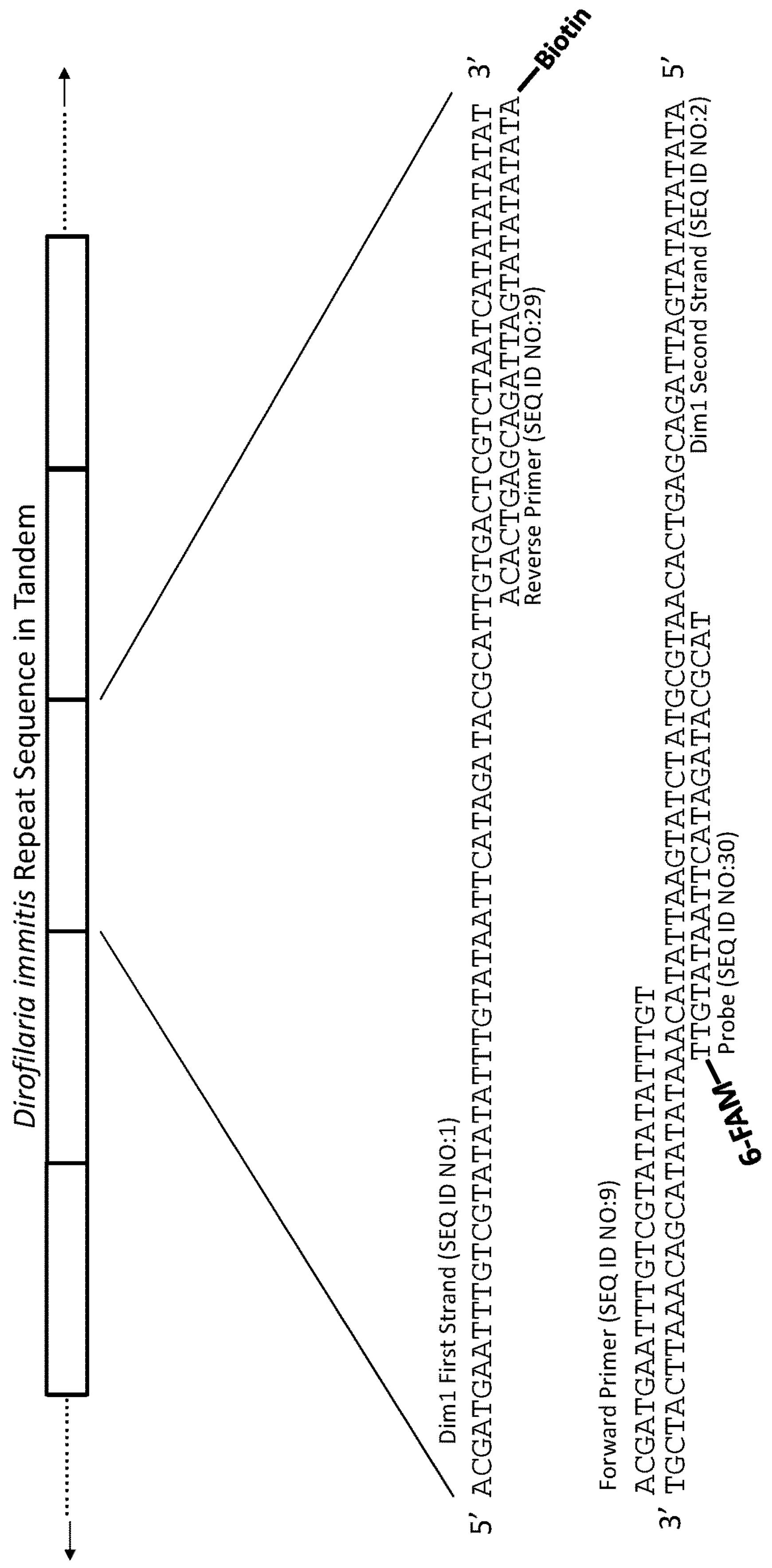
FIG. 5 shows exemplary test strip primer and probe set p4Dim1 hybridized to *D. immitis* repetitive target DNA Dim1 in accordance with an embodiment of the present invention. All forward primers and probes are 5' to 3'. All reverse primers are 3' to 5'.

Briefly, tissue sample from a mammal, or a mosquito pool, suspected of being infected with *D. immitis* or *D. repens* is subject to PCR using primers specific for target DNA, e.g., Dim1 or Dre1, respectively. One or both of the PCR primers is labeled with a conjugation moiety that is able to bind to the band on the test strip. For example, as shown in FIG. 5, reverse primer SEQ ID NO:29 is labeled with a biotin conjugation moiety. After PCR amplification of target DNA Dim1 using this reverse primer, the strand of DNA that was synthesized from SEQ ID NO:29 during PCR is biotin-labeled and this DNA strand may then be bound to a test strip having a band coated with streptavidin. After binding of the PCR product to the test strip band, a test strip probe(s) is then hybridized to a complementary sequence on the band-bound DNA strand. The test strip probe is labeled with a moiety to facilitate its detection. For example, in FIG. 5, test strip probe SEQ ID NO:30 is labeled with 6-FAM. In some embodiments, the presence of this hybridized probe may be visualized using anti-FITC antibodies conjugated to gold particles (anti-FITC antibodies bind specifically to 6-FAM). Thus, if target parasite DNA is present in the tissue sample, DNA strands synthesized during PCR of the target DNA from PCR primers having a conjugation moiety bind to the test strip band; if bound to the test strip band, a test strip probe will hybridize to a complementary sequence on the band-bound DNA; and if the test strip probe hybridizes to the band-bound DNA, its presence may be visualized, for example, through the use of antibodies that bind the label of the test strip probe. If no target parasite DNA is present in the tissue sample, no DNA will bind to the test strip band and visualization will not occur.

As discussed above, various conjugation moieties and capture media chemistries may be used other than biotin/streptavidin.

Moreover, test strip probes may include detectable labels other than 6-FAM. Suitable labels include, but are not limited to 5' TET, 5' Yakima Yellow®, 5' HEX, 5' JOE, 5' Cy3, 5' Texas Red-X®, 5' Cy5, 5' MAX, 5' TYE 563, 5' TAMRA, 5' ROX. 5' TEX 615, and 5' TYE 665.

In addition, the presence of a test strip probe may be visualized other than through the use of gold particle-conjugated antibodies that specifically bind the label of the test strip probe. For example, alkaline phosphatase-conjugated antibodies that specifically bind the label of the test strip probe may be used with a colorimetric peroxidase substrate for visualization.

In some embodiments, capture oligonucleotides may be used to capture target DNA from the tissue sample prior to PCR of target DNA for strip test detection of the presence of target DNA. In other embodiments, capture oligonucleotides are not used prior to PCR of target DNA for strip test detection of the presence of target DNA.

In some embodiments, kits are provided that are suitable for detecting a *D. immitis* infection in an animal host comprising a set of test strip PCR primers, at least one of which has a conjugation moiety, a test strip probe, each primer and probe being complementary to repetitive species-specific *D. immitis* target DNA, capture media that binds DNA synthesized from a PCR primer having a conjugation moiety, and a set of written instructions for detecting the *D. immitis* infection. At least one PCR primer of the set may be biotinylated and the capture media may be coated with streptavidin. The capture media may include a test strip having a band that is coated with a reactive group that binds the conjugation moiety.

In some embodiments, kits are provided that are suitable for detecting a *D. repens* infection in an animal host comprising a set of test strip PCR primers, at least one of which has a conjugation moiety, a test strip probe, each primer and probe being complementary to repetitive species-specific *D. repens* target DNA, capture media that binds DNA synthesized from a PCR primer having a conjugation moiety, and a set of written instructions for detecting the *D. repens* infection. At least one PCR primer of the set may be biotinylated and the capture media may be coated with streptavidin. The capture media may include a test strip having a band that is coated with a reactive group that binds the conjugation moiety.

Materials and Methods

The following exemplary materials and methods may be used in accordance with embodiments of the invention. One skilled in the art will appreciate that the following materials and methods are merely exemplary, and that these protocols may adjusted as needed to provide for specific circumstances.

Assay Design

Assay designs described herein involve using next-generation sequencing (NGS) of a parasite genome, e.g., the genome of *D. immitis* or *D. repens*, followed by use of a bioinformatics pipeline to identify the most highly repeated DNA elements found in the genome of the parasite species in question. This pipeline is then used to filter data on highly repeated DNA elements in order to identify those that have a DNA sequence that is specific to the parasite species in question. Using these highly repeated, species-specific DNA sequences, we then utilize the bioinformatics pipeline to design optimal capture oligonucleotides for genomic parasite target DNA comprising the repetitive species-specific sequence, and to design optimal PCR primers and probe sets to detect the captured target DNA.

Target DNA Sequence Identification

Paired end next-generation sequencing-based analysis of DNA extracted from adult parasites is performed using the Illumina MiSeq® platform [300 cycle cartridge (2×150)]. In some embodiments, other NGS sequencing platforms, known to those of skill in the art, may also be used. Following analysis, raw reads are trimmed and filtered, such that all reads are of equal length (those reads less than 100 bases in length are removed and all reads greater than 100 bases are trimmed such that they are 100 bases in length). Paired-end reads are then interlaced and a subset of reads (between 500,000 and 1,000,000) are analyzed using the Galaxy-based/RepeatExplorer and TAREAN software tools (Novák P, et al. *Bioinformatics.* 29, 6, 2013; Novak P, et al. *Nucleic Acids Res.* 45, 12, 2017. These programs allow for an all-to-all BLAST analysis during which each read is compared to every other read within the data set. Pairs are formed when any two reads share 90% or greater similarity over 55% or more of the read lengths, and read pairs are then used to build clusters of reads meeting these criteria. When building clusters, each read is represented by a node, and a successful pairing is depicted by the presence of an edge connecting two nodes. The length of the edge is characteristic of the similarity between the two reads, with a shorter edge connecting two reads that have greater identity and a longer edge representing two reads that, while still meeting the criteria for pairing, are less similar. Based on the length of edges and the relationships of the individual nodes, clusters then take on characteristic shapes. As such, shorter repeats form tighter, star-burst-like clusters (Grant J R et al. *Front Genet.* 10, 833, 2019) because individual reads within the cluster meet the pair-forming criteria with a larger number of other reads in the cluster. In addition to visual observation of cluster structure, connectivity can be further assessed by looking at the connected component index, which is the ratio of the number of pairs within a cluster compared with the maximum number of possible pairs. For example, if every read within a cluster met the pair-forming criterion with every other read in the cluster, the connected component index would be 1.00. Thus, a greater connected component index indicates a greater degree of sequence conservation among the reads in a cluster. This number, in combination with the total number of reads mapping to a cluster is then used to select candidate repeats for use as possible genomic parasite target DNA as these two factors allow for the selection of the genomic repeat elements of putatively greatest copy number. Superclusters can also be built when two or more clusters share high degrees of sequence similarity based on the presence of complementary paired-end read mates split between two clusters.

Following selection of candidate target repeat DNA sequences, NCBI-based BLAST analysis is performed to screen for, and eliminate, potential target repeat DNA sequences that are predicted to have significant similarity to DNA from other relevant organisms (for example, the host species, closely related parasite species, commensal bacteria found in the host, etc.). Through such screening, the likelihood of selecting parasite target DNA that will exhibit cross-reactivity with other species that might interfere with the specificity of the assay is greatly reduced. PrimerQuest software is then used to select possible primer/probe candidates to give optimal PCR amplification of the target repeat DNA element. These candidates are further screened using NCBI-based primer-BLAST analyses to further eliminate primer pairs that might result in relevant off-target PCR amplification.

Capture Oligonucleotide Design

A pair of 5' biotinylated capture oligonucleotides (SEQ ID NO:3 and SEQ ID NO:4) was designed to be complementary to each strand of the double-stranded *D. immitis* target DNA (Dim1) (FIG. 1A). This allows for the capture of both strands of the *D. immitis* target DNA.

Likewise, a pair of 5' biotinylated capture oligonucleotides (SEQ ID NO:7 and SEQ ID NO:8) was designed to be complementary to each strand of the double-stranded *D. repens* target DNA (Dre1) (FIG. 1B). This allows for the capture of both strands of the *D. repens* target DNA.

Canine Plasma Isolation from Collected Whole Blood Samples

Whole blood is collected in cell-free DNA BCT® Blood collection tubes (Streck, USA) and kept at room temperature until DNA isolation is initiated. Whole blood is centrifuged at 2,000×g for 20 minutes to isolate plasma. The recovered plasma is then centrifuged at 16,000×g for 10 minutes to pellet residual cells and debris. The supernatant is transferred to cryotubes and stored at −80° C. until processing.

Capture of Parasite cfDNA from Canine Plasma Samples

The input sample consists of 200 µl plasma+100 µl 1× binding buffer. (5 mM Tris-HCl (pH 7.5); 0.5 mM EDTA; 1M NaCl), 1.0 picomole of each biotinylated capture oligonucleotide is added and the sample is heated to 95° C. for 10 minutes to denature the cfDNA in the plasma sample. This step creates single-stranded cfDNA molecules exposing the complementary hybridization sites. The hybridization of the biotinylated capture oligonucleotides to the complementary cfDNA target takes place at 55° C. in a shaking incubator (750+ rpm). Bead capture of the cfDNA is achieved by adding 50 µl of streptavidin coated magnetic beads (Dynabeads™ M-270 Streptavidin, ThermoFisher) and allowing the sample to incubate at room temperature in a shaking incubator (900+ rpm) for 30 minutes. This step allows the cfDNA that has hybridized to the biotinylated capture oligonucleotides to bind to the streptavidin coated beads by a strong streptavidin-biotin linkage. A magnet is used to isolate the beads carrying the captured parasite cfDNA. The beads are washed twice with 1× binding buffer. Elution of the captured parasite cfDNA is accomplished by washing the beads in 1×SSC and then resuspending the beads in 50 µl dd$H_2O$ followed by an incubation at 95° C. for 5 minutes. This step elutes the non-biotinylated parasite cfDNA (the target DNA) into the water. A magnet is used to isolate the beads and recover the eluted cfDNA in solution. 50 µl of sample is recovered (FIG. 2).

Alternatively, the target DNA can be eluted from the beads using PCR amplification. Using this method, the beads are resuspended in 50 µl PCR mix (PCR reaction mix with the non-biotinylated parasite-specific PCR primer pair) and directly amplified (3-5 cycles). The supernatant now contains the non-biotinylated amplified parasite target DNA. A magnet is used to isolate the beads and the amplified target DNA is recovered from the solution.

Mosquito Pool Sample Preparation: Crude Extraction Technique

Briefly, in a 1.7 ml microfuge tube, a sterile plastic micro-pestle (Axygen Scientific, Union City, CA) is used to grind each mosquito pool (of up to 25 mosquitoes) with 180 µl of 0.2 N NaOH for 3 min. The micro-pestle is then rinsed with an additional 180 µl of 0.2 N NaOH into the same 1.7 ml tube containing the ground mosquitoes to be sure all mosquito debris is removed from the pestle. A new, clean, sterile micro-pestle is used for each pool. Each tube is incubated at 75° C. for 10 minutes. 115.2 µl of 1 M Tris (pH=8.0) and 364.8 µl of nuclease-free water are added to each sample and the tubes are thoroughly mixed using a vortex mixer for 10 seconds. Samples are centrifuged at 10,000×g for 3 minutes, and the supernatant, containing extracted DNA, is collected and transferred into a clean 1.7 ml microcentrifuge tube. See Zaky et al. *PLoS Negl Trop Dis.* 2018 Nov. 21; 12(11).

Mosquito Pool Sample Preparation: Column-Based Extraction Technique

Pools of up to 25 mosquitoes are placed in a 2.0 ml microcentrifuge tube. One or more zinc ball bearings (or similar item) is placed into each tube. 180 µl of phosphate-buffered saline (pH 7.2) is added to each tube. Tubes are vortexed on a horizontal shaking platform for 30 minutes. Each tube is centrifuged briefly to collect debris at the bottom of the tube. 20 μl of Proteinase K is added to each sample. 200 μl of a buffer containing chaotropic salts (such as Qiagen buffer AL) is then added to each sample and mixed by vortexing for 3 seconds. The tubes are then incubate for 10 minutes at 70° C. An additional 20 μl of Proteinase K is then added to each sample and mixed by vortexing for 3 seconds. Tubes are incubated for 1 hour at 56° C. and then centrifuged at at 16,000×g or greater for 5 minutes to pellet debris. The supernatant from each tube is transferred to a new tube and add 200 μl of 98% ethanol is added to each sample. Each sample is then applied to an ion exchange column or bead-based solution (such as the Qiagen DNeasy spin column) and centrifuged at 8,000×g for 1 minute. Flow through is discarded and 500 μl of ethanol-containing wash buffer (such as Qiagen buffer AW1) is added to each sample and centrifuged at 16,000×g or faster for 3 minutes. This ethanol wash is repeated twice more. After the final centrifugation, the column is transferred to a new, clean microcentrifuge tube and 25 μl or more of elution solution (e.g., nuclease-free water, phosphate-buffered saline, Tris-EDTA, or other like solution) is added to each column. Allow the elution solution to sit on the column for a minimum of 2 minutes. Centrifuge each column at 10,000×g for 2 minutes to elute the DNA-containing sample from the column. See Fischer, P, et al. *Ann Trop Med Parasitol.* 96: 809-821 (2002).

Detection of the Target DNA (*D. immitis*)

Three real-time PCR primer and probe sets (p1Dim1, p2Dim1, and p3Dim1) (Integrated DNA Technologies, Coralville, Iowa, USA) were designed to be complementary to the *D. immitis* Dim1 repeat target DNA.

For p1Dim1, the forward primer (SEQ ID NO:9) and probe (SEQ ID NO:11) are complementary to sequences on one DNA strand (SEQ ID NO:2) of the *D. immitis* repetitive Dim1 target DNA. The reverse primer (SEQ ID NO:10) is complementary to a sequence on the opposite DNA strand (SEQ ID NO:1) of the Dim1 repetitive target DNA (FIG. 3A). The probe has the fluorescent dye 6-FAM attached to its 5' terminus and the quencher IABkFQ attached to its 3' terminus. In addition, the probe has an internal ZEN™ quencher 9 bases from the 5' end. Real-time PCR examples herein use primer and probe set p1Dim1.

For p2Dim1, the forward primer (SEQ ID NO:9) and probe (SEQ ID NO:22) are complementary to sequences on one DNA strand (SEQ ID NO:2) of the *D. immitis* repetitive Dim1 target DNA. The reverse primer (SEQ ID NO:21) is complementary to a sequence on the opposite DNA strand (SEQ ID NO:1) of the Dim1 repetitive target DNA (FIG. 3B). The probe has the fluorescent dye 6-FAM attached to its 5' terminus and the quencher IABkFQ attached to its 3' terminus. In addition, the probe has an internal ZEN™ quencher 9 bases from the 5' end.

For p3Dim1, the forward primer (SEQ ID NO:9) and probe (SEQ ID NO:24) are complementary to sequences on one DNA strand (SEQ ID NO:2) of the *D. immitis* repetitive Dim1 target DNA. The reverse primer (SEQ ID NO:23) is complementary to a sequence on the opposite DNA strand (SEQ ID NO:1) of the Dim1 repetitive target DNA (FIG. 3C). The probe has the fluorescent dye 6-FAM attached to its 5' terminus and the quencher IABkFQ attached to its 3' terminus. In addition, the probe has an internal ZEN™ quencher 9 bases from the 5' end.

Thermal cycling was performed using the StepOnePlus Real-Time PCR System (Applied Biosystems, Foster City, CA). 20 μl real-time PCR reactions were set up with the following reagents: 10 μl of 2× TaqPath ProAmp Master Mix (ThermoFisher Scientific, Waltham, Massachusetts); 0.8 μl of 20 μM forward primer); 0.8 μl of 20 μM reverse primer; 2.5 μl of 1 μM probe; 0.9 μl of $ddH_2O$; and 5 μl of template DNA (e.g., eluted Dim1 target DNA). Real-time PCR cycling conditions were as follows: 2 minutes at 50° C. and then 10 minutes at 95° C., followed by 40 cycles of 15 seconds at 95° C. and 1 minute at 62° C.

Detection of the Target DNA (*D. repens*)

Three real-time PCR primer and probe sets (p1Dre1, p2Dre1, and p3Dre1) (Integrated DNA Technologies, Coralville, Iowa, USA) were designed to be complementary to the *D. repens* Dre1 repeat target DNA.

For p1Dre1, the forward primer (SEQ ID NO:12) and probe (SEQ ID NO:14) are complementary to sequences on one DNA strand (SEQ ID NO:6) of the *D. repens* repetitive Dre1 target DNA. The reverse primer (SEQ ID NO:13) is complementary to a sequence on the opposite DNA strand (SEQ ID NO:5) of the Dre1 repetitive target DNA (FIG. 3D). The probe has the fluorescent dye 6-FAM attached to its 5' terminus and the quencher IABkFQ attached to its 3' terminus. In addition, the probe has an internal ZEN™ quencher 9 bases from the 5' end.

For p2Dre1, the forward primer (SEQ ID NO:15) and probe (SEQ ID NO:17) are complementary to sequences on one DNA strand (SEQ ID NO:6) of the *D. repens* repetitive Dre1 target DNA. The reverse primer (SEQ ID NO:16) is complementary to a sequence on the opposite DNA strand (SEQ ID NO:5) of the Dre1 repetitive target DNA (FIG. 3E). The probe has the fluorescent dye 6-FAM attached to its 5' terminus and the quencher IABkFQ attached to its 3' terminus. In addition, the probe has an internal ZEN™ quencher 9 bases from the 5' end.

For p3Dre1, the forward primer (SEQ ID NO:18) and probe (SEQ ID NO:20) are complementary to sequences on one DNA strand (SEQ ID NO:6) of the *D. repens* repetitive Dre1 target DNA. The reverse primer (SEQ ID NO:19) is complementary to a sequence on the opposite DNA strand (SEQ ID NO:5) of the Dre1 repetitive target DNA (FIG. 3F). The probe has the fluorescent dye 6-FAM attached to its 5' terminus and the quencher IABkFQ attached to its 3' terminus. In addition, the probe has an internal ZEN™ quencher 9 bases from the 5' end.

Thermal cycling is performed using the StepOnePlus Real-Time PCR System (Applied Biosystems, Foster City, CA). For each of the three primer and probe sets (p1Dre1, p2Dre1, and p3Dre1), 20 μl real-time PCR reactions are set up with the following reagents: 10 μl of 2× TaqPath ProAmp Master Mix; 0.8 μl of 20 μM forward primer; 0.8 μl of 20 μM reverse primer; 2.5 μl of 1 μM probe; 0.9 μl of $ddH_2O$; and 5 μl of template DNA (e.g., eluted Dre1 target DNA). Real-time PCR cycling conditions are as follows: 2 minutes at 50° C. and then 10 minutes at 95° C., followed by 40 cycles of 15 seconds at 95° C. and 1 minute at 60° C.

DNA Capture/Isolation for Strip Assay

Total cfDNA is isolated from canine plasma using the Thermofisher MagMAX™ Cell-Free DNA Isolation Kit following the manufacturer's instructions. For each canine sample, 2 ml of plasma was used as starting material with an elution volume of 30 μl. 5 μl of eluate was used as template for each PCR reaction using primers SEQ ID NO:9 and SEQ ID NO:29 (35 cycles).

Alternatively, parasite-specific cfDNA may be captured using capture oligonucleotides bound to a capture medium, e.g., an appropriately coated magnetic bead surface that binds the capture oligonucleotides. The oligonucleotides may first be bound to an appropriately treated capture medium, followed by hybridization to the target DNA, e.g., Dim1. The target DNA may be eluted from the beads using PCR amplification with strip test PCR primers (SEQ ID NO:9 and SEQ ID NO:29) (35 cycles).

PCR Amplification for Strip Assay

Thermal cycling was performed using the StepOnePlus Real-Time PCR System (Applied Biosystems, Foster City, CA). Each PCR reaction was set up as follow: 25 μl of 2× TaqPath ProAmp Master Mix; 1 μl of 10 μM forward primer (SEQ ID NO:9); 1 μl of 10 μM biotinylated reverse primer (SEQ ID NO:29); 5 μl of eluate (template); and 18 μl of $ddH_2O$. PCR cycling conditions are as follows: 10 minutes at 95° C., followed by 35 cycles of 40 seconds at 95° C. and 1 minute at 60° C., and a single 10 minute extension at 60° C.

Detection for Strip Assay

10 μl of PCR product is combined with 1 μl of 10 pmol/μl strip test probe (SEQ ID NO:30) and 39 μl of annealing buffer (10 mM Tris, pH 7.5-8, 50 mM NaCl and 1 mM EDTA). The PCR product is then denatured by heating the mixture to 95° C. for 5 minutes. The mixture is then held at 55° C. for 30 minutes to hybridize the strip test probe to the biotinylated DNA strand of the PCR product.

The test strip was next exposed to the mixture and, through lateral flow, the mixture migrated through the length of the test strip. A visible positive result occurs when the biotinylated strand, hybridized to the 6-FAM-labeled probe, binds to a band on the test strip (capture medium) that is streptavidin-coated. Gold-labeled anti-fluorescein (6-FAM) antibodies, which bind to the 6-FAM-labeled probe, allow for the visualization of the Dim1 PCR product on the test strip. See Zaky et al. *PLoS Negl Trop Dis.* 2018 Nov. 21; 12(11).

Example 1

Analytical Sensitivity of the Dim1 *D. immitis* Real-Time PCR Assay

The analytical sensitivity of the Dim1 *D. immitis* real-time PCR assay was first assessed using the p1Dim1 primer and probe set with serially diluted amounts of *D. immitis* genomic DNA as template (100 picograms, 10 picograms, 1 picogram, 100 femtograms, 10 femtograms, 1 femtogram, 100 attograms, 10 attograms, and 1 attogram). All reactions were carried out with five replicates. Real-time amplification of the *D. immitis* DNA is indicated by the cycle number when the probe fluorescence was detected at the threshold as indicated by the cycle quantification (Cq) values. Results are considered positive when amplification occurs with a mean Cq value of less than 40. Mean Cq and standard deviation (SD) of five replicates for each input amount of genomic DNA are shown in Table 1. The *D. immitis* real-time PCR assay consistently detected *D. immitis* genomic DNA in all replicates down to 10 attograms of input *D. immitis* genomic DNA. However, only two out of five replicates showed *D. immitis* DNA detection at 1 attogram of input template DNA. According to these data, analytical sensitivity of the *D. immitis* Dim1 real-time PCR assay is determined to be between 10 attograms and 1 attograms of *D. immitis* genomic DNA.

TABLE 1

| Genomic DNA Amount | 100 pg | 10 pg | 1 pg | 100 fg | 10 fg | 1 fg | 100 ag | 10 ag | 1 ag | No Template Control |
|---|---|---|---|---|---|---|---|---|---|---|
| Mean Cq (SD) | 15.78 (0.12) | 19.25 (0.05) | 22.69 (0.11) | 26.47 (0.35) | 30.0277 (0.6) | 33.1844 (1.55) | 33.4076 (1.6) | 34.5652 (1.41) | 34.872 (0.48) | Un-detected |

Example 2

Species-Specificity of the Dim1 *D. immitis* Real-Time PCR Assay

The species-specificity of the Dim1 *D. immitis* real-time PCR assay was demonstrated using genomic DNA from various closely related filarial parasites along with canine and feline genomic DNA. 100 pg of input genomic DNA from the following parasites was used as template: *Brugia malayi, Loa loa, Brugia pahangi, Acanthocheilonema viteae, Wuchereria bancrofti, Onchocerca volvulus* and *Onchocerca ochengi*. Canine and feline genomic DNA (10 nanograms, 1 nanogram, and 100 picograms) were used as template to test for cross-reactivity with these mammalian host species' genomic DNA. No signal was detected in all samples tested demonstrating no cross-reactivity of the Dim1 assay with a variety of available parasite, canine, and feline DNA samples (Table 2).

TABLE 2

| Genomic DNA (gDNA) Template | Mean Cq |
|---|---|
| *Brugia malayi* gDNA (100 pg) | Undetected |
| *Loa loa* gDNA (100 pg) | Undetected |
| *Onchocerca ochengi* gDNA (1 ng) | Undetected |
| *Onchocerca volvulus* gDNA (100 pg) | Undetected |
| *Brugia pahangi* gDNA (100 pg) | Undetected |
| *Acanthocheilonema viteae* gDNA (100 pg) | Undetected |
| *Wuchereria bancrofti* gDNA (100 pg) | Undetected |
| Canine gDNA (10 ng) | Undetected |
| Canine gDNA (1 ng) | Undetected |
| Canine gDNA (100 pg) | Undetected |
| Feline gDNA (10 ng) | Undetected |
| Feline gDNA (1 ng) | Undetected |
| Feline gDNA (100 pg) | Undetected |
| *D. immitis* gDNA (10 pg) Positive Control | 16.659 |

Example 3

Comparison of Sensitivity Between Dim1 Real-Time PCR Assay and Two Current PCR Assays A comparison of amplification efficiency between our *D. immitis* assay (Dim1 real-time PCR assay) and two current real-time PCR assays, one targeting the *D. immitis* mitochondrial Cytochrome C Oxidase Subunit 1 ("mitochondrial COI") gene (Tahir et. al. *Veterinary Parasitology* 235, 1-7 (2017)) and the other targeting the *D. immitis* 16S ribosomal RNA ("16S rRNA") gene (Watts et. al. *Molecular and Cellular Probes* 14, 425-430 (1999)), was conducted using

*D. immitis* genomic DNA as the template. Each sample was tested in triplicate. Resulting mean Cq values demonstrate that our Dim1 real-time PCR assay detected *D. immitis* genomic DNA 5.6 cycles earlier (using 10 pg input DNA) and 6.5 cycles earlier (using 1 pg input DNA) during amplification compared to the mitochondria COI assay (Table 3). Likewise, the Dim1 real-time PCR assay detected *D. immitis* genomic DNA about 4 cycles earlier across all amounts of input DNA (100 pg, 10 pg, and 1 pg) compared to the 16S rRNA assay (Table 4). These data indicate an increase in sensitivity of the *D. immitis* Dim1 real-time PCR assay compared to both the mitochondria COI and 16S rRNA real-time PCR assays. This increase in sensitivity was about 65-fold compared to the mitochondrial COI assay and about 16-fold compared to the 16S rRNA assay.

TABLE 3

| | *D. immitis* gDNA (10 pg) | *D. immitis* gDNA (1 pg) |
|---|---|---|
| Dim1 Assay (Mean Cq) | 19.9 | 24.75 |
| Mitochondrial COI Assay (Mean Cq) | 25.58 | 31.33 |

TABLE 4

| | *D. immitis* gDNA (100 pg) | *D. immitis* gDNA (10 pg) | *D. immitis* gDNA (1 pg) |
|---|---|---|---|
| Dim1 Assay (Mean Cq) | 15.7 | 19.2 | 22.6 |
| 16S rRNA Assay (Mean Cq) | 19.7 | 23.4 | 26.8 |

Example 4

Comparison of Limits of Detection Between Dim1 Real-Time PCR Assay and Two Currently Used Assays A comparison of the analytical limits of detection of our Dim1 real-time PCR assay with the currently used 16S rRNA assay and the currently used mitochondrial COI assay was performed using serially diluted *D. immitis* genomic DNA as template (10 picograms, 1 picogram, 100 femtograms, 10 femtograms, 1 femtogram, 100 attograms, 10 attograms, 1 attogram, and 100 zeptograms). Consistent detection (indicated by an "X" in Table 5) is determined by a Cq value below 40 in at least 2 out of 3 replicate reactions. As shown in Table 5, our Dim1 real-time PCR assay shows consistent detection to 10 ag of *D. immitis* genomic DNA, while the 16S rRNA assay and the mitochondrial COI assay show consistent detection to 1 fg of *D. immitis* genomic DNA. This data illustrates that the analytical sensitivity of Dim1 real-time PCR assay detection is approximately 100-fold greater than currently used real-time PCR assays. Therefore, the *D. immitis* Dim1 real-time PCR assay can provide increased sensitivity of detection for pre-patent infections in canine and feline patient samples.

TABLE 5

| *D. immitis* gDNA | Dim1 Assay | 16S rRNA Assay | Mitochondrial COI Assay |
|---|---|---|---|
| 10 pg | X | X | X |
| 1 pg | X | X | X |
| 100 fg | X | X | X |
| 10 fg | X | X | X |
| 1 fg | X | X | X |
| 100 ag | X | | |
| 10 ag | X | | |
| 1 ag | | | |
| 100 zg | | | |

Example 5

Evaluation of Dim1 Real-Time PCR Assay on Canine Blood Samples

Our Dim1 assay was validated with clinical samples from infected and uninfected canine whole blood samples. Briefly, DNA was isolated from 300 μl of canine whole blood using the Qiagen DNeasy Blood and Tissue DNA column extraction kit following the manufacturer's instructions. DNA was eluted in 75 μl $ddH_2O$ and 1 μl was used for each Dim1 real-time PCR assay. Data shows no detection of *D. immitis* DNA in four uninfected canines and three *Brugia pahangi* infected canines (Table 6). *B. pahangi* is a closely related filarial nematode parasite. Therefore, no false positives or cross-reactivity with the feline/canine parasite *B. pahangi* was observed. In addition, no detection of *D. immitis* was seen in two canines infected with fifty L3 *D. immitis* larvae 2.5 months prior to blood collection (Table 6). These two canines have an early pre-patent infection with no detectable microfilariae in the blood. The *D. immitis* parasite normally develops into an immature adult and first enters the bloodstream approximately 70 days post-infection [Kotani, T. & Powers, K. G. *Am. J. Vet. Res.* 43, 2199-2206 (1982)]. Therefore, detection of *D. immitis* DNA in whole blood samples at 2.5 months post-infection was not necessarily expected since this would be shortly after the first worms would reach the bloodstream. Detection at high levels was seen in four canines that were exhibiting patent infections with *D. immitis* (Table 6). The *D. immitis* Dim1 real-time PCR assay performed as expected with clinical samples showing no detection in unexposed canines and early pre-patent canines, no cross-reactivity in *Brugia pahangi* infected canines, and strong detection in canines with patent infections and high microfilaria counts in blood samples.

TABLE 6

| Canine Blood Sample | Microfilaria (mf) Count | Mean Cq (SD) |
|---|---|---|
| Unexposed Canine #1 | 0 mf/ml | Undetected |
| Unexposed Canine #2 | 0 mf/ml | Undetected |
| Unexposed Canine #3 | 0 mf/ml | Undetected |
| Unexposed Canine #4 | 0 mf/ml | Undetected |
| *Brugia pahangi* Infected Canine #5 | 6,700 mf/ml | Undetected |
| *Brugia pahangi* Infected Canine #6 | 1,000 mf/ml | Undetected |
| *Brugia pahangi* Infected Canine #7 | 125 mf/ml | Undetected |
| *D. immitis* Infected Canine #8 Pre-patent 2.5 Months | 0 mf/ml | Undetected |
| *D. immitis* Infected Canine #9 Pre-patent 2.5 Months | 0 mf/ml | Undetected |
| *D. immitis* Infected Canine #10 | 32,000 mf/ml | 7.96 (0.05) |
| *D. immitis* Infected Canine #11 | 5,525 mf/ml | 12.40 (0.05) |

TABLE 6-continued

| Canine Blood Sample | Microfilaria (mf) Count | Mean Cq (SD) |
|---|---|---|
| *D. immitis* Infected Canine #12 | 15,100 mf/ml | 9.34 (0.11) |
| *D. immitis* Infected Canine #13 | 34,925 mf/ml | 8.29 (0.07) |

Example 6

Sensitivity of Dim1 Real-Time PCR Assay in Detecting Pre-Patent Infections Using Cell-Free DNA Clinical sensitivity of our Dim1 real-time PCR assay in detecting pre-patent *D. immitis* infections was assessed in two infected canines (canine #8 and canine #9) using cell-free DNA (cfDNA) isolated from plasma. During the pre-patent period, *D. immitis* worms start as L3 larvae (the infective stage from the mosquito) and later enter the host bloodstream as immature adults approximately 70 days post-infection. Once these immature adults are in the bloodstream, they can shed cells and DNA into the host bloodstream. Patency is achieved approximately 6-7 months after infection, at which time these infections can be detected by current standard serology techniques identifying an antigen shed by the sexually mature adult females. During the pre-patent period, the adult female antigen is not present or not present in a high enough concentration to be detected by current serologic techniques. However, DNA shed from the immature adult worms is present in the bloodstream as cell-free DNA (cfDNA) during this pre-patent period. We have demonstrated that *D. immitis* DNA, as part of the total cfDNA fraction, can be detected in clinical pre-patent infections using our *D. immitis* Dim1 real-time PCR assay. Briefly, whole blood was collected from each of the canines every two weeks starting at three months post-infection with fifty *D. immitis* third stage larvae (L3). Total cfDNA was isolated from canine plasma using the Thermofisher MagMAX™ Cell-Free DNA Isolation Kit following the manufacturer's instructions. At each time point and for each canine, 2 μl of isolated DNA was used as starting material with an elution volume of 30 μl. For our Dim1 real-time PCR assay, 5 μl of eluate was used as template for each PCR reaction and each sample was tested in triplicate.

The data shows that in each of the two artificially infected canines, *D. immitis* cfDNA was detected using our Dim1 real-time PCR assay in plasma samples from all time points as indicated by mean Cq values less than 40 (Table 7). Serological antigen detection of infection using a current standard point-of-care device (DiroCHEK® antigen test (Zoetis, Parsippany, NJ)) was shown to first occur at 5 months post-infection and 5.5 months post-infection for canine #8 and canine #9, respectively, in heat-treated serum (heat treatment of serum has been demonstrated to improve DiroCHEK assay sensitivity). In non-heat-treated serum, serological detection of antigen was shown to first occur at 5 months post-infection and 7.5 months post-infection for canine #8 and canine #9, respectively.

As shown in Table 7, *D. immitis* cfDNA was clearly detected in the plasma, prior to serological detection of antigen, at 3 months, 3.5 months, 4 months and, 4.5 months post-infection as indicated by Cq values less than 40. These results demonstrate the ability of our *D. immitis* Dim1 real-time PCR assay to detect pre-patent infections in canines 2+ months prior to antigen detection of infection. This has important implications for successful early drug treatment prior to patency.

TABLE 7

| Months Post-Infection | Canine # 8 Mean Cq | Canine # 9 Mean Cq |
|---|---|---|
| 3 months | 34.52 | 36.52 |
| 3.5 months | 35.16 | 38.9 |
| 4 months | 33.98 | 32.54 |
| 4.5 months | 35.4 | 34.5 |
| 5 months | 30.78 | 32.2 |
| 5.5 months | 26.58 | 28.35 |
| 6 months | 21.34 | 25.39 |
| 6.5 months | 24.59 | 23.22 |
| 7 months- (became patent) [microfilariae count] | 23.62 [275 mf/ml] | 23.48 [25 mf/ml] |
| 7.5 months | 22.2 | 21.5 |

To assess if our *D. immitis* Dim1 real-time PCR assay could produce false positive detection of cfDNA from canine plasma, two unexposed canines and two *B. pahangi* infected canines were tested. As shown in Table 8, the data show no signal was detected in any of the samples, indicating no false positive detection and no cross-reactivity/detection with the feline/canine parasite *B. pahangi*.

TABLE 8

| Sample | Mean Cq |
|---|---|
| Unexposed Canine #1 | Undetected |
| Unexposed Canine #3 | Undetected |
| *Brugia pahangi* Infected Canine #5 | Undetected |
| *Brugia pahangi* Infected Canine #6 | Undetected |

Example 7

Use of Magnetic Nanoparticle Technology and Oligonucleotides to Capture *D. immitis* Dim1 Target DNA in Buffer We assessed the ability of magnetic nanoparticle technology (magnetic beads) coupled with biotin-modified *D. immitis*-specific capture oligonucleotides to efficiently capture *D. immitis* DNA in solution. To mimic positive canine samples, 100 pg of *D. immitis* genomic DNA (gDNA) (sample 1) and 100 pg each of *D. immitis* genomic gDNA and canine gDNA (sample 2) were added to 200 μl of 1 M salt binding buffer. A set of 5' biotinylated capture oligonucleotides were used to specifically target and hybridize to *D. immitis* gDNA in solution. Each capture oligonucleotide of the pair is designed to be complementary to opposing DNA strands within the *D. immitis* Dim1 target DNA repeat, allowing the capture of both strands of *D. immitis* DNA. Isolation of the captured DNA is achieved by biotin-streptavidin linkages to streptavidin coated magnetic beads (Dynabeads™ M-270 Streptavidin, ThermoFisher) thereby linking the Dim1 target DNA to the beads (FIG. 2). Once eluted, the isolated DNA sample is enriched for the *D. immitis* Dim1 target DNA. The recovered DNA was detected by our Dim1 repeat real-time PCR assay and the results were compared to a standard curve of known amounts of input *D. immitis* gDNA (FIG. 4).

As shown in Table 9, the data show amplification and detection of recovered *D. immitis* gDNA in both test samples as indicated by Cq values of 19.98 and 20.44 respectively. For each sample, the mean Cq value is the mean of five replicates per sample.

Figure 4:
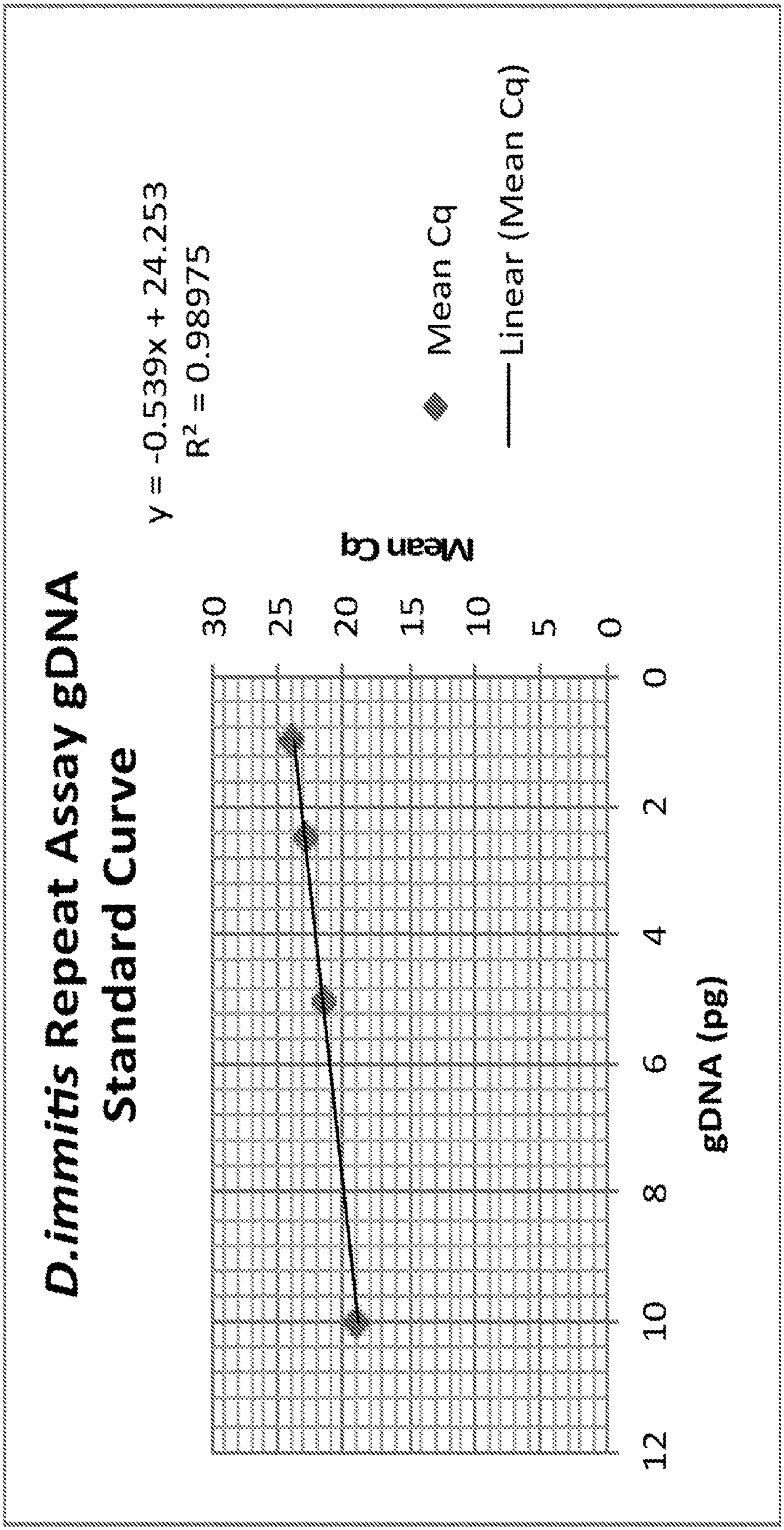
FIG. 4 shows a real-time PCR standard curve for *D. immitis* gDNA generated using primer and probe set p1Dim1 in accordance with an embodiment of the present invention.

To determine the amount of DNA recovered from solution, we performed our *D. immitis* Dim1 real-time PCR assay using 10 picograms, 5 picograms, 2.5 picograms, and 1 picogram of input *D. immitis* gDNA and a standard curve was generated using mean Cq values (FIG. 4). Using the best fit line formula, DNA recovery was determined to be 7.9 picograms per 5 μl input template volume (Table 9 Sample 1) and 7.1 picogram per 5 μl input template volume (Table 9 Sample 2). Given a 50 μl total DNA recovery volume for each sample, the total recovery is calculated to be 79 picograms and 71 picograms, respectively. These data show that the DNA capture method recovered 79% of *D. immitis* DNA from Table 9 Sample 1 (100 pg added *D. immitis* DNA) and 71% of *D. immitis* DNA from Table 9 Sample 2 (100 pg added *D. immitis* DNA and 100 pg canine DNA). These results validate the ability of the DNA capture method to efficiently recover specific DNA sequences from solution.

Furthermore, this specific capture method facilitates the enrichment of *D. immitis* target DNA that yields optimal sensitivity of detection with our Dim1 real-time PCR assay.

TABLE 9

| Sample | Mean Cq (SD) |
|---|---|
| 10 pg *D. immitis* gDNA | 18.96 (0.07) |
| 5 pg *D. immitis* gDNA | 21.42 (0.22) |
| 2.5 pg *D. immitis* gDNA | 22.69 (0.18) |
| 1 pg *D. immitis* gDNA | 23.97 (0.19) |
| (Table 9 Sample 1) 1M Salt Buffer + *D. immitis* gDNA (100 pg) | 19.98 (0.12) |
| (Table 9 Sample 2) 1M Salt Buffer + *D. immitis* and Canine gDNA (100 pg) | 20.44 (0.03) |

Example 8

Use of Magnetic Nanoparticle Technology and Oligonucleotides to Capture *D. immitis* Dim1 Target DNA from Canine Plasma We further assessed the ability of the magnetic nanoparticle (magnetic bead) technology coupled with biotin-modified *D. immitis*-specific capture oligonucleotides to efficiently capture *D. immitis* DNA from plasma. To mimic a positive canine plasma sample, 100 pg of *D. immitis* gDNA was added to 200 μl of plasma derived from an unexposed canine. A 1× binding buffer supplemented with 100 pg each of *D. immitis* and canine DNA was used as a comparison of total DNA recovery. As shown in Table 10, data show the amplification and detection of recovered *D. immitis* DNA in both test samples as indicated by Cq values of 19.79 (plasma sample) and 20.52 (1 M salt buffer), respectively. This data represents a Cq difference of less than 1 indicating similar recovery of input DNA in both samples. This method is therefore capable of efficiently capturing parasite DNA from plasma.

TABLE 10

| Sample | Mean Cq (SD) |
|---|---|
| 1M Salt Buffer + *D. immitis* and Canine gDNA (100 pg) | 20.52 (0.68) |
| Unexposed Plasma + *D. immitis* gDNA (100 pg) | 19.79 (0.59) |

Example 9

Sensitivity of Dim1 Real-Time PCR Assay in Detecting Patent Infections Using Cell-Free DNA Clinical sensitivity of an embodiment of our Dim1 real-time PCR assay in detecting patent microfilaria positive *D. immitis* infections was assessed in three *D. immitis* infected canines (canine #14, canine #15, and canine #16) using cell-free DNA ("cfDNA") isolated from canine plasma. Total cfDNA was isolated from canine plasma using the Thermofisher MagMAX™ Cell-Free DNA Isolation Kit (ThermoFisher, Waltham, Massachusetts, USA) following the manufacturer's instructions. At each time point and for each canine, 2 ml of plasma was used as starting material with an elution volume of 30 μl. 5 μl of eluate was used as template for each real-time PCR reaction using primer and probe set p1Dim1 and each sample was tested in triplicate.

As shown in Table 11, *D. immitis* cfDNA was clearly detected in the plasma in patent microfilaria positive canines. These results demonstrate the presence of *D. immitis* cfDNA in the plasma samples of canines with patent infections and high microfilaria counts.

TABLE 11

| Sample | Microfilaria (mf) Count | Mean Cq (SD) |
|---|---|---|
| *D. immitis* infected Canine #14 | 28,000 mf/ml | 29.75 (0.45) |
| *D. immitis* infected Canine #15 | 6,000 mf/nl | 30.29 (0.15) |
| *D. immitis* infected Canine #16 | 28,000 mf/ml | 19.06 (0.02) |
| *D. immitis* gDNA 10 pg (positive control) | N/A | 19.42 (0.07) |

Example 10

Strip Test Detection of Dim1 Repetitive Target DNA (SEQ ID NO:2)

Strip test detection sensitivity of *D. immitis* repetitive species-specific target DNA was assessed using the primer and probe set p4Dim1 (SEQ ID NO:9, SEQ ID NO:29, SEQ ID NO:30) (FIG. 5) with serially diluted amounts of *D. immitis* genomic DNA as template (1 picogram, 100 femtograms, 10 femtograms, 1 femtogram, 100 attograms, 10 attograms, 1 attogram, 100 zeptograms). Briefly, PCR was performed using forward and reverse primers, SEQ ID NO:9 and SEQ ID NO:29, respectively, for 35 cycles. One DNA strand of the PCR product will be biotinylated after PCR amplification—the strand synthesized from biotinylated PCR primer SEQ ID NO:29. The PCR product is denatured (95° C. for 5 minutes) and the 6-FAM-labeled probe (SEQ ID NO:30) is added to hybridize to the biotinylated DNA strand. Through lateral flow, the sample migrates through the length of the test strip. A visible positive result occurs when the biotinylated strand, hybridized to the 6-FAM-labeled probe, binds to a band on the test strip (capture medium) that is streptavidin-coated. Gold-labeled anti-fluorescein (6-FAM) antibodies, which bind to the 6-FAM-labeled probe, allow for the visualization of the Dim1 PCR product on the test strip.

Figure 6A:
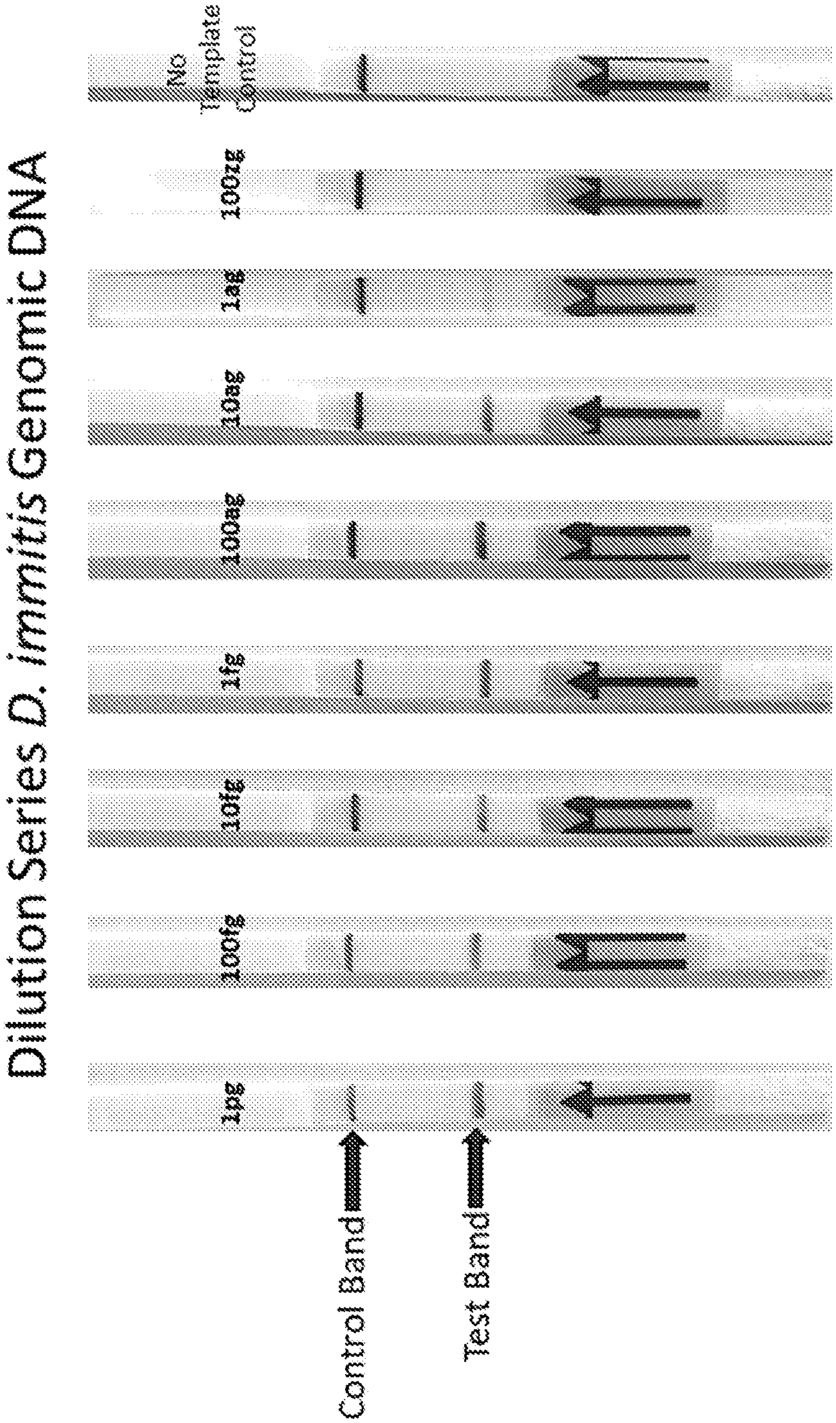
FIGS. 6A to 6C show test strip PCR results in accordance with embodiments of the present invention.

The data show that the strip detection method consistently detected *D. immitis* genomic DNA down to 1 attogram of input *D. immitis* genomic DNA (FIG. 6A). According to these data, analytical sensitivity of the strip detection method is comparable to an embodiment of the Dim1 *D.*

*immitis* real-time PCR assay, with an analytical sensitivity between 10 and 1 attograms of input *D. immitis* genomic DNA. (Table 1).

Our Dim1 strip test detection assay was validated with clinical samples from infected and uninfected canine plasma samples. Briefly, total cfDNA was isolated from canine plasma using the Thermofisher MagMAX™ Cell-Free DNA Isolation Kit following the manufacturer's instructions. For each canine sample, 2 ml of plasma was used as starting material with an elution volume of 30 μl. 5 μl of eluate was used as template for each PCR reaction using primer and probe set p4Dim1 (35 cycles).

Alternatively, parasite-specific cfDNA can be captured using capture oligonucleotides bound to a capture medium, e.g., an appropriately coated magnetic bead surface that binds the capture oligonucleotides. The oligonucleotides may first be bound to an appropriately treated capture medium, followed by hybridization to the target DNA, e.g., Dim1. The target DNA may be eluted from the beads using PCR amplification with strip primers (SEQ ID NO:9 and SEQ ID NO:29) (35 cycles). This supernatant now contains the PCR product comprising one biotinylated strand. A magnet may be used to remove the beads and the amplified target DNA can be recovered and tested using the strip, as set forth above.

In either instance, the PCR product can be denatured (95° C. for 5 minutes) and the strip test probe, e.g., SEQ ID NO:30, may be added to hybridize to the biotinylated DNA strand. As described, above, through lateral flow, the sample migrates through the length of the test strip. A visible positive result occurs when the biotinylated strand, hybridized to the 6-FAM-labeled probe, binds to a band on the test strip (capture medium) that is streptavidin-coated. Gold-labeled anti-fluorescein (6-FAM) antibodies, which bind to the 6-FAM-labeled probe, allow for the visualization of the Dim1 PCR product on the test strip.

Figure 6C:
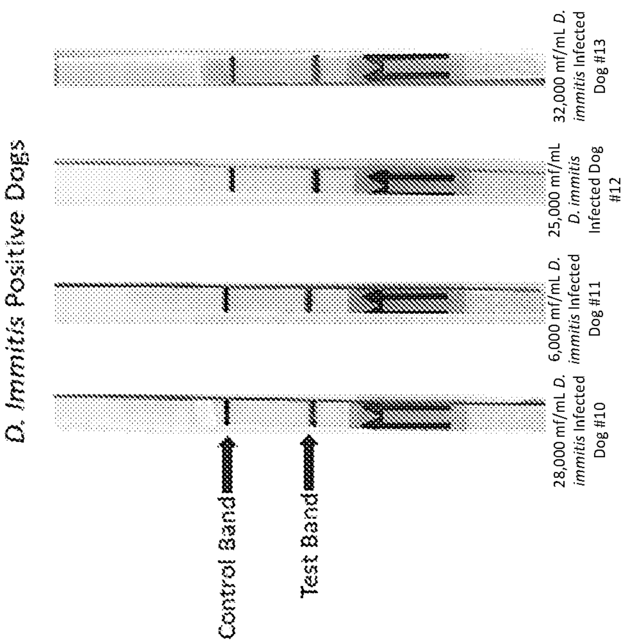
Figure 6B:
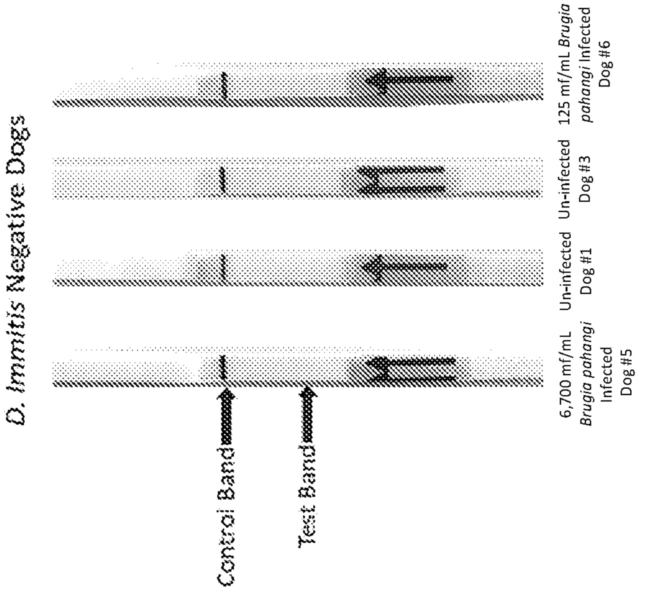

The strip test detection assay performed as expected with clinical samples, showing no detection in unexposed canines, no cross-reactivity in *Brugia pahangi* infected canines, and strong detection in canines with patent infections and high microfilaria counts in blood samples (FIGS. 6B and 6C). See also, Zaky et al. *PLoS Negl Trop Dis.* 2018 Nov. 21; 12(11).

REFERENCES

Akter, S., Nakao, R., Imasato, Y., Alam, M. Z. & Katakura, K. Potential of cell-free DNA as a screening marker for parasite infections in dog. *Genomics* 111, 906-912 (2019).

Albonico, F. et al. Rapid differentiation of *Dirofilaria immitis* and *Dirofilaria repens* in canine peripheral blood by real-time PCR coupled to high resolution melting analysis. *Vet. Parasitol.* 200, 128-132 (2014).

Capelli, G. et al. Recent advances on *Dirofilaria repens* in dogs and humans in Europe. *Parasites and Vectors* 11, 1-21 (2018).

Ciuca, L. et al. Heat treatment of serum samples from stray dogs naturally exposed to *Dirofilaria immitis* and *Dirofilaria repens* in Romania. *Vet. Parasitol.* 225, 81-85 (2016).

Dantas-Torres, F. & Otranto, D. Dirofilariosis in the Americas: A more virulent *Dirofilaria immitis? Parasites and Vectors* 6, 1 (2013).

Genchi, C. & Kramer, L. Subcutaneous dirofilariosis (*Dirofilaria repens*): An infection spreading throughout the old world. *Parasites and Vectors* 10, 1-6 (2017).

Genchi, C. & Kramer, L. H. The prevalence of *Dirofilaria immitis* and *D. repens* in the Old World. *Vet. Parasitol.* 280, 108995 (2019).

Gioia, G. et al. Highly sensitive multiplex PCR for simultaneous detection and discrimination of *Dirofilaria immitis* and *Dirofilaria repens* in canine peripheral blood. *Vet. Parasitol.* 172, 160-163 (2010).

Haddock, K. C. Canine heartworm disease: A review and pilot study. *Soc. Sci. Med.* (1987).

Harizanov, R. N., Jordanova, D. P. & Bikov, I. S. Some aspects of the epidemiology, clinical manifestations, and diagnosis of human dirofilariasis caused by *Dirofilaria repens. Parasitol. Res.* 113, 1571-1579 (2014).

Knight, D. H. Heartworm infection. *Veterinary Clinics of North America—Small Animal Practice* (1987).

Kotani, T. & Powers, K. G. Developmental stages of *Dirofilaria immitis* in the dog. *Am. J. Vet. Res.* 43, 2199-2206 (1982).

Latrofa, M. S. et al. A duplex real-time polymerase chain reaction assay for the detection of and differentiation between *Dirofilaria immitis* and *Dirofilaria repens* in dogs and mosquitoes. *Vet. Parasitol.* 185, 181-185 (2012).

Little, S., Saleh, M., Wohltjen, M. & Nagamori, Y. Prime detection of *Dirofilaria immitis*: Understanding the influence of blocked antigen on heartworm test performance. *Parasites and Vectors* 11, 1-10 (2018).

Monchy, D., Levenes, H., Guegan, H., Poey, C. & Dubourdieu, D. Pulmonary dirofilariasis. *Médecine tropicale: revue du Corps de santé colonial* (1993).

Norgen Biotek. *Dirofilaria immitis* PCR Detection Kit. (2011).

Otranto, D. et al. Dirofilariosis in the Americas: A more virulent *Dirofilaria immitis? Parasites and Vectors* 6, 1 (2013).

Pilotte N., Maasch J. R. M. A., Easton A. V., Dahlstrom E., Nutman T. B. & Williams S. A. Targeting a highly repeated germline DNA sequence for improved real-time PCR-based detection of *Ascaris* infection in human stool. *PLoS Negl Trop Dis.* 13, 7 (2019).

Pilotte N, Unnasch T. R. & Williams S. A. The Current Status of Molecular Xenomonitoring for Lymphatic Filariasis and Onchocerciasis. *Trends Parasitol.* 33, 10 (2017).

Ro, J. Y. et al. Pulmonary dirofilariasis: The great imitator of primary or metastatic lung tumor. A clinicopathologic analysis of seven cases and a review of the literature. *Human Pathology* (1989).

Shearer, P. Literature Review—Heartworm Disease. *Banf Appl. Res. Knowl. Team* 1-16 (2011).

Silaghi, C., Beck, R., Capelli, G., Montarsi, F. & Mathis, A. Development of *Dirofilaria immitis* and *Dirofilaria repens* in *Aedes japonicus* and *Aedes geniculatus. Parasites and Vectors* 10, 1-13 (2017).

Tahir, D. et al. Molecular survey of *Dirofilaria immitis* and *Dirofilaria repens* by new real-time TaqMan® PCR assay in dogs and mosquitoes (Diptera: Culicidae) in *Corsica* (France). *Vet. Parasitol.* 235, 1-7 (2017).

Trancoso, T. A. L. et al. Detection of *Dirofilaria immitis* using microscopic, serological and molecular techniques among dogs in Cabo Frio, RJ, Brazil. *Rev Bras Parasitol Vet.* 29, 1, (2020).

Wang, D. et al. Factors influencing U.S. canine heartworm (*Dirofilaria immitis*) prevalence. *Parasites and Vectors* 7, 1-18 (2014).

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes: P1. A device for diagnosis of a parasite infection in an animal host, the device comprising;

a PCR measurement apparatus, including a thermocycler, the PCR measurement apparatus configured to target a repetitive sequence in DNA of the parasite in a tissue sample obtained from the infected animal host.

P2. A device according to claim P1, wherein the parasite is selected from the group consisting of *Dirofilaria immitis* and *Dirofilaria repens*.

P3. A device according to any one of claims P1-P2, wherein the repetitive sequence has been selected to provide sensitivity and selectivity to the parasite.

P4. A device according to any one of claims P1-P3, wherein the PCR measurement apparatus includes an optical readout mechanism.

P5. A device according to claim P4, wherein the accompanying optical readout mechanism includes a test strip having a visible band.

P6. A device according to any one of claims P1-P5, wherein the tissue sample is selected from the group consisting of plasma, serum, and whole blood obtained from the infected animal host.

P7. A device according to any one of claims P1-P6, wherein the tissue sample is from an infected mosquito.

P8. A method of treating a mammalian host suspected of being infected with a parasite, the method comprising:
- (a) providing a sample from the mammalian host suspected of being infected with the parasite; and
- (b) causing detecting presence of the parasite in the sample, the detecting including:
  - (i) making DNA available from the sample;
  - (ii) mixing the sample with a labeled DNA complementary to a target DNA; and
  - (iii) detecting the target DNA using PCR;
  - wherein, if the presence of the parasite has been detected as a result of causing detecting, administrating to the mammalian host a treatment effective at reducing or eliminating the parasite infection.

P9. A method according to claim P8, wherein the labeled DNA has been made using processes including:
- a. identifying the target DNA, wherein the target DNA is repetitive DNA uniquely possessed by the parasite, the identifying including:
  - i. obtaining genomic DNA sequence reads from the parasite,
  - ii. trimming each sequence read to produce a read set of trimmed sequence reads of equal length,
  - iii. comparing each sequence of the read set to all of the other sequence reads in the read set in order to form read pairs, wherein each read of a given pair shares with the other read of the pair at least 90% similarity over at least 55% of its length,
  - iv. evaluating the read pairs to identify in the genome of the parasite a candidate set of sequences having putatively a high copy number in the genome, and
  - v. selecting from the candidate set of sequences a final sequence uniquely possessed by the parasite; and
- b. causing synthesis of the labeled DNA using the final sequence uniquely possessed by the parasite,
- wherein the labeled DNA is complementary to the identified repetitive DNA uniquely possessed by the parasite.

P10. A method according to any one of claims P8-P9, wherein the parasite is selected from the group consisting of *D. immitis* and *D. repens*.

P11. A method according to claim P10, wherein the parasite infection is patent.

P12. A method according to claim P10, wherein the parasite infection is pre-patent.

P13. A method according to any one of claims P8-P12, wherein the tissue sample is selected from the group consisting of plasma, serum, and whole blood obtained from the infected mammalian host.

P14. A method according to any one of claims P8-P13, wherein the mammalian host is a canine.

P15. A method according to any one of claims P8-P14, wherein the labeled DNA comprises a conjugation moiety.

P16. A method according to claim P15, wherein the conjugation moiety is biotin.

P17. A method according to any one of claims P8-P16, wherein the target DNA is isolated from the mixture using a capture medium that binds a capture DNA.

P18. A method according to claim P17, wherein the capture medium is selected from the group consisting of a magnetic bead and a test strip.

P19. A method according to any one of claims P17-P18, wherein the capture medium is coated with streptavidin.

P20. A method according to any one of claims P8-P19, wherein the PCR is real-time PCR using a primer and probe set.

P21. A method according to claim P20, wherein the parasite is *D. immitis* and the primer and probe set is selected from the group consisting of p1Dim1, p2Dim1, and p3Dim1.

P22. A method according to claim P20, wherein the parasite is *D. repens* and the primer and probe set is selected from the group consisting of p1Dre1, p2Dre1, and p3Dre1.

P23. A method according to any one of claims P8-P21, wherein the parasite is *D. immitis* and the target DNA is Dim1.

P24. A method according to any one of claims P8-P21 and P23, wherein the parasite is *D. immitis* and the labeled DNA is a set of capture oligonucleotides consisting of SEQ ID NO:3 and SEQ ID NO:4.

P25. A method according to any one of claims P8-P20 and P22, wherein the parasite is *D. repens* and the target DNA is Dre1.

P26. A method according to any one of claims P8-P20, P22, and P25, wherein the parasite is *D. repens* and the labeled DNA is a set of capture oligonucleotides consisting of SEQ ID NO:7 and SEQ ID NO:8.

P27. A method according to any one of claims P8-P26, wherein the treatment is selected from the group consisting of melarsomine, ivermectin, doxycycline, moxidectin, and combinations thereof.

P28. A kit for detecting a parasite infection in an animal host comprising, a) labeled DNA complementary to repetitive species-specific parasite target DNA, b) a capture medium that binds a capture DNA, and c) a set of written instructions for detecting the parasite infection.

P29. A kit according to claim P28, wherein the parasite is selected from the group consisting of *D. immitis* and *D. repens.*

P30. A kit according to any one of claims P28-P29, wherein the labeled DNA comprises a conjugation moiety.

P31. A kit according to claims P30, wherein the conjugation moiety is biotin.

P32. A kit according to any one of claims P28-P31, wherein the capture medium is selected from the group consisting of a magnetic bead, a test strip, and combinations thereof.

P33. A kit according to any one of claim P28-P32, wherein the capture medium is coated with streptavidin.

P34. A kit according to any one of claims P28-P33, wherein the kit comprises a primer and probe set.

P35. A kit according to any one of claims P28-P34, wherein the parasite is *D. immitis* and the labeled DNA is a set of capture oligonucleotides consisting of SEQ ID NO:3 and SEQ ID NO:4.

P36. A kit according to any one of claims P28-P35, wherein the parasite is *D. immitis* and the target DNA is Dim1.

P37. A kit according to claim P34, wherein the parasite is *D. immitis* and the primer and probe set is selected from the group consisting of p1Dim1, p2Dim1, p3Dim1, and p4Dim1.

P38. A kit according to any one of claims P28-P34, wherein the parasite is *D. repens* and the labeled DNA is a set of capture oligonucleotides consisting of SEQ ID NO:7 and SEQ ID NO:8.

P39. A kit according to any one of claims P28-P34 and P38, wherein the parasite is *D. repens* and the target DNA is Dre1.

P40. A kit according to claim P34, wherein the parasite is *D. repens* and the primer and probe set is selected from the group consisting of p1Dre1, p2Dre1, and p3Dre1.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A kit for detecting a *Dirofilaria immitis* infection in an animal host comprising, (a) a capture oligonucleotide component, wherein the capture oligonucleotide component consists of a set of capture oligonucleotides, the set consisting of:

(i) a first capture oligonucleotide complementary to SEQ ID NO: 1; and (ii) a second capture oligonucleotide complementary to SEQ ID NO: 2, wherein the first capture oligonucleotide and the second capture oligonucleotide each comprise a non-nucleic acid conjugation moiety; and (b) a capture medium, wherein the capture medium has a surface, the surface having a non-nucleic acid coating that specifically binds the non-nucleic acid conjugation moiety, thereby configuring the capture medium to selectively bind the set of capture oligonucleotides consisting of the first capture oligonucleotide and the second capture oligonucleotide, wherein the capture oligonucleotide component includes all capture oligonucleotides in the kit.

2. The kit according to claim 1, wherein the non-nucleic acid conjugation moiety is biotin.

3. The kit according to claim 1, wherein the capture medium is selected from the group consisting of a magnetic bead, a test strip, and combinations thereof.

4. The kit according to claim 1, wherein the non-nucleic acid coating is streptavidin.

5. The kit according to claim 1, wherein the kit comprises a primer and labeled probe set.

6. The kit according to claim 1, wherein the first capture oligonucleotide is SEQ ID NO:3 and the second capture oligonucleotide is SEQ ID NO:4.

7. The kit according to claim 5, wherein the primer and labeled probe set is selected from the group consisting of:

primers SEQ ID NO:9 and SEQ ID NO: 10, and labeled probe SEQ ID NO: 11;

primers SEQ ID NO:9 and SEQ ID NO:21, and labeled probe SEQ ID NO:22;

primers SEQ ID NO:9 and SEQ ID NO:23, and labeled probe SEQ ID NO:24; and primers SEQ ID NO:9 and SEQ ID NO:29, and labeled probe SEQ ID NO:30.

8. The kit according to claim 3, wherein the non-nucleic acid conjugation moiety is biotin.

9. The kit according to claim 3, wherein the non-nucleic acid coating is streptavidin.

10. The kit according to claim 3, wherein the kit comprises a primer and probe set.

11. The kit according to claim 3, wherein the first capture oligonucleotide is SEQ ID NO:3 and the second capture oligonucleotide is SEQ ID NO:4.

12. The kit according to claim 10, wherein the primer and labeled probe set is selected from the group consisting of:

primers SEQ ID NO:9 and SEQ ID NO: 10, and labeled probe SEQ ID NO: 11;

primers SEQ ID NO:9 and SEQ ID NO:21, and labeled probe SEQ ID NO:22;

primers SEQ ID NO:9 and SEQ ID NO:23, and labeled probe SEQ ID NO:24; and primers SEQ ID NO:9 and SEQ ID NO:29, and labeled probe SEQ ID NO:30.

13. The kit according to claim 5, wherein the non-nucleic acid conjugation moiety is biotin.

14. The kit according to claim 5, wherein the capture medium is selected from the group consisting of a magnetic bead, a test strip, and combinations thereof.

15. The kit according to claim 5, wherein the non-nucleic acid coating is streptavidin.

16. The kit according to claim 5, wherein the first capture oligonucleotide is SEQ ID NO:3 and the second capture oligonucleotide is SEQ ID NO:4.

* * * * *

SEQUENCE LISTING

```
<160> NUMBER OF SEQ ID NOS: 30

<210> SEQ ID NO 1
<211> LENGTH: 71
<212> TYPE: DNA
<213> ORGANISM: Dirofilaria immitis

<400> SEQUENCE: 1

acgatgaatt tgtcgtatat atttgtataa ttcatagata cgcattgtga ctcgtctaat      60

catatatata t                                                           71


<210> SEQ ID NO 2
<211> LENGTH: 71
<212> TYPE: DNA
<213> ORGANISM: Dirofilaria immitis

<400> SEQUENCE: 2

atatatatat gattagacga gtcacaatgc gtatctatga attatacaaa tatatacgac      60

aaattcatcg t                                                           71


<210> SEQ ID NO 3
<211> LENGTH: 26
<212> TYPE: DNA
<213> ORGANISM: Artificial Sequence
<220> FEATURE:
<223> OTHER INFORMATION: 5'-biotin

<400> SEQUENCE: 3

acgatgaatt tgtcgtatat atttgt                                           26


<210> SEQ ID NO 4
<211> LENGTH: 21
<212> TYPE: DNA
<213> ORGANISM: Artificial Sequence
<220> FEATURE:
<223> OTHER INFORMATION: 5'-biotin
```

<400> SEQUENCE: 4
tgattagacg agtcacaatg c 21

<210> SEQ ID NO 5
<211> LENGTH: 211
<212> TYPE: DNA
<213> ORGANISM: Dirofilaria repens

<400> SEQUENCE: 5
ttggtaataa gacttaataa attttaatct caaatatttc cttgttaata tatctggtgt 60
tctattgtta tatatattcc ggtagaccat gaaatgatgt ttttattatt gtacattatc 120
aaactctggt aaaccaaatg tccaagaacc gatgcattaa atgaaaacag aaaccttggt 180
aataagactt aataaatttt aatctcaaat a 211

<210> SEQ ID NO 6
<211> LENGTH: 211
<212> TYPE: DNA
<213> ORGANISM: Dirofilaria repens

<400> SEQUENCE: 6
tatttgagat taaaatttat taagtcttat taccaaggtt tctgttttca tttaatgcat 60
cggttcttgg acatttggtt taccagagtt tgataatgta caataataaa aacatcattt 120
catggtctac cggaatatat ataacaatag aacaccagat atattaacaa ggaaatattt 180
gagattaaaa tttattaagt cttattacca a 211

<210> SEQ ID NO 7
<211> LENGTH: 26
<212> TYPE: DNA
<213> ORGANISM: Artificial Sequence
<220> FEATURE:
<223> OTHER INFORMATION: 5'-biotin

<400> SEQUENCE: 7
tccttgttaa tatatctggt gttcta 26

<210> SEQ ID NO 8
<211> LENGTH: 22
<212> TYPE: DNA
<213> ORGANISM: Artificial Sequence
<220> FEATURE:
<223> OTHER INFORMATION: 5'-biotin

<400> SEQUENCE: 8
ggttcttgga catttggttt ac 22

<210> SEQ ID NO 9
<211> LENGTH: 26
<212> TYPE: DNA
<213> ORGANISM: Artificial Sequence
<220> FEATURE:
<223> OTHER INFORMATION: Synthetic construct

<400> SEQUENCE: 9
acgatgaatt tgtcgtatat atttgt 26

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
tgattagacg agtcacaatg c 21

<210> SEQ ID NO 11
<211> LENGTH: 26
<212> TYPE: DNA
<213> ORGANISM: Artificial Sequence
<220> FEATURE:
<223> OTHER INFORMATION: 5'-6-FAM fluorescent dye 3'-Iowa Black FQ quencher Internal ZEN quencher 9 bases from the 5' end

<400> SEQUENCE: 11
tcatagatac gcattgtgac tcgtct 26

<210> SEQ ID NO 12
<211> LENGTH: 26
<212> TYPE: DNA
<213> ORGANISM: Artificial Sequence
<220> FEATURE:
<223> OTHER INFORMATION: Synthetic construct

<400> SEQUENCE: 12
tccttgttaa tatatctggt gttcta 26

<210> SEQ ID NO 13
<211> LENGTH: 22
<212> TYPE: DNA
<213> ORGANISM: Artificial Sequence
<220> FEATURE:
<223> OTHER INFORMATION: Synthetic construct

<400> SEQUENCE: 13
ggttcttgga catttggttt ac 22

<210> SEQ ID NO 14
<211> LENGTH: 30
<212> TYPE: DNA
<213> ORGANISM: Artificial Sequence
<220> FEATURE:
<223> OTHER INFORMATION: 5'-6-FAM fluorescent dye 3'-Iowa Black FQ quencher Internal ZEN quencher 9 bases from the 5' end

<400> SEQUENCE: 14
tatattccgg tagaccatga aatgatgttt 30

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
ttccggtaga ccatgaaatg 20

<210> SEQ ID NO 16
<211> LENGTH: 24
<212> TYPE: DNA
<213> ORGANISM: Artificial Sequence
<220> FEATURE:
<223> OTHER INFORMATION: Synthetic construct

<400> SEQUENCE: 16
gtcttattac caaggtttct gttt 24

<210> SEQ ID NO 17
<211> LENGTH: 30
<212> TYPE: DNA
<213> ORGANISM: Artificial Sequence
<220> FEATURE:
<223> OTHER INFORMATION: 5'-6-FAM fluorescent dye 3'-Iowa Black FQ
      quencher Internal ZEN quencher 9 bases from the 5' end

<400> SEQUENCE: 17
cattatcaaa ctctggtaaa ccaaatgtcc 30

<210> SEQ ID NO 18
<211> LENGTH: 28
<212> TYPE: DNA
<213> ORGANISM: Artificial Sequence
<220> FEATURE:
<223> OTHER INFORMATION: Synthetic construct

<400> SEQUENCE: 18
ctattgttat atatattccg gtagacca 28

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
gcatcggttc ttggacatt 19

<210> SEQ ID NO 20
<211> LENGTH: 29
<212> TYPE: DNA
<213> ORGANISM: Artificial Sequence
<220> FEATURE:
<223> OTHER INFORMATION: 5'-6-FAM fluorescent dye 3'-Iowa Black FQ
      quencher Internal ZEN quencher 9 bases from the 5' end

<400> SEQUENCE: 20
attgtacatt atcaaactct ggtaaacca 29

<210> SEQ ID NO 21
<211> LENGTH: 21
<212> TYPE: DNA
<213> ORGANISM: Artificial Sequence
<220> FEATURE:
<223> OTHER INFORMATION: Synthetic construct

<400> SEQUENCE: 21
cgagtcacaa tgcgtatcta t 21

<210> SEQ ID NO 22
<211> LENGTH: 24
<212> TYPE: DNA
<213> ORGANISM: Artificial Sequence
<220> FEATURE:
<223> OTHER INFORMATION: 5'-6-FAM fluorescent dye 3'-Iowa Black FQ
      quencher Internal ZEN quencher 9 bases from the 5' end

<400> SEQUENCE: 22
acgcattgtg actcgtctaa tcat 24

<210> SEQ ID NO 23
<211> LENGTH: 26
<212> TYPE: DNA

```
<213> ORGANISM: Artificial Sequence
<220> FEATURE:
<223> OTHER INFORMATION: Synthetic construct

<400> SEQUENCE: 23

atatatatat gattagacga gtcaca                                          26


<210> SEQ ID NO 24
<211> LENGTH: 29
<212> TYPE: DNA
<213> ORGANISM: Artificial Sequence
<220> FEATURE:
<223> OTHER INFORMATION: 5'-6-FAM fluorescent dye 3'-Iowa Black FQ
      quencher Internal ZEN quencher 9 bases from the 5' end

<400> SEQUENCE: 24

aattcataga tacgcattgt gactcgtct                                       29


<210> SEQ ID NO 25
<211> LENGTH: 61
<212> TYPE: DNA
<213> ORGANISM: Dirofilaria repens

<400> SEQUENCE: 25

atggatagaa tagatatata tgtataaata taattttcaa tattatttat acatgatgta     60

t                                                                     61


<210> SEQ ID NO 26
<211> LENGTH: 131
<212> TYPE: DNA
<213> ORGANISM: Dirofilaria repens

<400> SEQUENCE: 26

tagcttcgtt ggttttccct aagtcacgaa ttgctcctat caaaggtatg actattccaa     60

gattagagtt attagccgtg ctcataggaa tacgtggtgc tcaatttgtt attaaacaga    120

tgaaatagaa a                                                         131


<210> SEQ ID NO 27
<211> LENGTH: 361
<212> TYPE: DNA
<213> ORGANISM: Dirofilaria repens

<400> SEQUENCE: 27

ttaattttct ctgtgccttc tatgatgtta ttcaatgtcg tgatgatgct tctttttaca     60

gtattaagaa tcttttatta attttatccg tgcattctat gatgttattc agtgtcgtga    120

tgatgcttct ttttacagta ttaagaattt ttctacttta ttgttttaga aattgtatga    180

gttttttttg tgccttctat gatgttattc agtgtcgtga tgatgcttct ttttgcagta    240

ttaagaatat ttcttttatt aattttctct gtgccttcta tgatgttatt cagtgtcgtg    300

atgatgcttc tttttacagt attaagaatt tttcttttat taattttctc tgtgccttct    360

a                                                                    361


<210> SEQ ID NO 28
<211> LENGTH: 354
<212> TYPE: DNA
<213> ORGANISM: Dirofilaria repens

<400> SEQUENCE: 28

tttcctatat ataaaatcct atatttaaat aattaattga taaaattaaa tcctatattt     60
```

-continued

```
cctatatata aaatcctata tttaaattat ttgattgata aaattaaatc ctatatttcc    120

tatatataaa atcctattta aattatttga ttgataaaat taaatcctat atttcctata    180

tataaaatcc tatatttaaa ttatttgatt gataaaatta aatcctatat ttcctatata    240

taaaatccta tatttaaata attaattgat aaaattaaat cctatatttc ctatatataa    300

aatcctatat ttaaattatt tgattgataa aattaaatcc tatatttcct atat          354


<210> SEQ ID NO 29
<211> LENGTH: 26
<212> TYPE: DNA
<213> ORGANISM: Artificial Sequence
<220> FEATURE:
<223> OTHER INFORMATION: 5'-biotin

<400> SEQUENCE: 29

atatatatat gattagacga gtcaca                                          26


<210> SEQ ID NO 30
<211> LENGTH: 23
<212> TYPE: DNA
<213> ORGANISM: Artificial Sequence
<220> FEATURE:
<223> OTHER INFORMATION: 5' 6-FAM fluorescent dye

<400> SEQUENCE: 30

ttgtataatt catagatacg cat                                             23
```